United States Patent
Morita

(10) Patent No.: US 10,278,664 B2
(45) Date of Patent: May 7, 2019

(54) TOMOGRAPHIC IMAGE GENERATION DEVICE, METHOD AND RECORDING MEDIUM

(71) Applicant: FUJIFILM Corporation, Tokyo (JP)

(72) Inventor: Junya Morita, Ashigarakami-gun (JP)

(73) Assignee: FUJIFILM CORPORATION, Minato-Ku, Tokyo (JP)

( * ) Notice: Subject to any disclaimer, the term of this patent is extended or adjusted under 35 U.S.C. 154(b) by 0 days.

(21) Appl. No.: 15/274,727

(22) Filed: Sep. 23, 2016

(65) Prior Publication Data
US 2017/0086770 A1  Mar. 30, 2017

(30) Foreign Application Priority Data
Sep. 29, 2015 (JP) ................................. 2015-190658

(51) Int. Cl.
*A61B 6/00* (2006.01)
*A61B 6/03* (2006.01)

(52) U.S. Cl.
CPC ............ *A61B 6/5258* (2013.01); *A61B 6/032* (2013.01); *A61B 6/5264* (2013.01); *A61B 6/5282* (2013.01)

(58) Field of Classification Search
CPC ..... A61B 6/032; A61B 6/5258; A61B 6/5264; A61B 6/5282
See application file for complete search history.

(56) References Cited

U.S. PATENT DOCUMENTS

| | | | |
|---|---|---|---|
| 6,674,835 B2 * | 1/2004 | Kaufhold | A61B 5/4869 378/207 |
| 7,761,135 B2 * | 7/2010 | Pfister | A61B 6/12 382/128 |
| 7,991,106 B2 * | 8/2011 | Ren | A61B 6/025 378/21 |

(Continued)

FOREIGN PATENT DOCUMENTS

| JP | 2007-050264 A | 3/2007 |
|---|---|---|
| JP | 2010-119437 A | 6/2010 |

(Continued)

OTHER PUBLICATIONS

Communication dated Nov. 20, 2018 issued by the Japanese Patent Office in counterpart application No. 2015-190658.

*Primary Examiner* — Brenda C Bernardi
(74) *Attorney, Agent, or Firm* — Sughrue Mion, PLLC

(57) ABSTRACT

A first image obtaining unit obtains a plurality of projection images corresponding to different radiation source positions, the projection images being imaged under a first imaging condition for tomosynthesis imaging, and a second image obtaining unit obtains a two-dimensional image imaged with a given radiation source position under a second imaging condition for simple imaging. An image quality correction unit performs image quality correction on the projection images to compensate for a difference of image quality between the projection images and the two-dimensional image based on a difference between the first imaging condition and the second imaging condition. A reconstruction unit reconstructs the projection images having been subjected to the image quality correction and the two-dimensional image to generate a tomographic image of a slice plane of the subject.

12 Claims, 13 Drawing Sheets

(56) References Cited

U.S. PATENT DOCUMENTS

| | | | |
|---|---|---|---|
| 8,000,435 B2* | 8/2011 | Bertram | G06T 11/005 378/6 |
| 8,180,018 B2* | 5/2012 | Sawada | A61B 6/00 378/11 |
| 8,340,373 B2* | 12/2012 | Claus | G06T 11/006 378/4 |
| 8,447,088 B2* | 5/2013 | Kanagawa | A61B 6/025 378/4 |
| 8,634,627 B2* | 1/2014 | Fujisawa | A61B 6/032 128/922 |
| 2009/0123052 A1 | 5/2009 | Ruth et al. | |
| 2009/0202127 A1* | 8/2009 | Bertram | G06T 11/005 382/131 |
| 2010/0124312 A1 | 5/2010 | Enomoto et al. | |
| 2011/0060566 A1* | 3/2011 | Bertram | G06T 11/005 703/2 |
| 2011/0075793 A1 | 3/2011 | Akahori et al. | |
| 2012/0134464 A1* | 5/2012 | Hoernig | A61B 6/025 378/22 |
| 2012/0140878 A1 | 6/2012 | Souchay | |
| 2012/0195403 A1 | 8/2012 | Vedantham et al. | |
| 2012/0238870 A1* | 9/2012 | Smith | A61B 6/025 600/431 |
| 2013/0004041 A1 | 1/2013 | Yang et al. | |
| 2013/0044861 A1* | 2/2013 | Muller | A61B 6/025 378/62 |
| 2013/0051516 A1* | 2/2013 | Yang | A61B 6/03 378/4 |
| 2014/0376691 A1* | 12/2014 | Hoernig | G06T 11/006 378/37 |
| 2015/0003591 A1* | 1/2015 | Schweizer | A61B 6/481 378/62 |
| 2015/0093013 A1 | 4/2015 | Morita | |
| 2015/0157282 A1 | 6/2015 | Kobayashi et al. | |
| 2015/0379711 A1 | 12/2015 | Imai | |
| 2016/0007943 A1* | 1/2016 | Hoernig | A61B 6/482 378/37 |
| 2016/0012616 A1* | 1/2016 | Hoernig | G06T 11/005 378/37 |
| 2016/0081645 A1* | 3/2016 | Fukuda | A61B 6/5205 378/4 |
| 2016/0189376 A1* | 6/2016 | Bernard | G06T 11/006 382/132 |
| 2016/0206264 A1* | 7/2016 | Fukuda | A61B 6/025 |
| 2016/0235385 A1 | 8/2016 | Enomoto et al. | |
| 2017/0042496 A1* | 2/2017 | Shanbhag | A61B 5/055 |
| 2017/0065241 A1* | 3/2017 | Hoernig | A61B 6/025 |

FOREIGN PATENT DOCUMENTS

| | | | | |
|---|---|---|---|---|
| JP | 2010158299 A | * | 7/2010 | A61B 6/00 |
| JP | 2011-087917 A | | 5/2011 | |
| JP | 2012-115677 A | | 6/2012 | |
| JP | 2012-512669 A | | 6/2012 | |
| JP | 2012-157551 A | | 8/2012 | |
| JP | 2014-014655 A | | 1/2014 | |
| JP | 2014-207958 A | | 11/2014 | |
| JP | 2015-089429 A | | 5/2015 | |
| JP | 2015-131096 A | | 7/2015 | |

* cited by examiner

| BREAST THICKNESS [mm] | SIMPLE IMAGING | | | TOMOSYNTHESIS IMAGING | | |
|---|---|---|---|---|---|---|
| | T/F | TUBE VOLTAGE [kV] | GRID | T/F | TUBE VOLTAGE [kV] | GRID |
| 0-20 | W/Rh | 26 | IN | W/Al | 26 | OUT |
| 20-30 | W/Rh | 27 | IN | W/Al | 28 | OUT |
| 30-40 | W/Rh | 28 | IN | W/Al | 30 | OUT |
| 40-50 | W/Rh | 29 | IN | W/Al | 32 | OUT |
| 50-60 | W/Rh | 30 | IN | W/Al | 34 | OUT |
| 60-70 | W/Rh | 31 | IN | W/Al | 36 | OUT |
| 70-80 | W/Rh | 32 | IN | W/Al | 38 | OUT |
| 80- | W/Rh | 33 | IN | W/Al | 40 | OUT |

| W/Rh | 20 | 40 | 60 | 80 | LUT2 |
|---|---|---|---|---|---|
| 23 | 1.03 | 0.93 | 0.87 | 0.83 | |
| 25 | 0.93 | 0.84 | 0.78 | 0.75 | |
| 27 | 0.90 | 0.81 | 0.76 | 0.72 | |
| 29 | 0.87 | 0.79 | 0.73 | 0.69 | |
| 31 | 0.85 | 0.76 | 0.70 | 0.65 | |
| 33 | 0.82 | 0.72 | 0.65 | 0.60 | |
| 35 | 0.78 | 0.68 | 0.60 | 0.54 | |

→ THICKNESS[mm]

↓ TUBE VOLTAGE[kV]

FIG.20

LUT3

|  | T/F | TUBE VOLTAGE | RADIATION DOSE | GRID | AGD |
|---|---|---|---|---|---|
| SIMPLE IMAGING | W/Rh | 29kV | 90mAs | IN | 1.00mGy |
| TOMOSYNTHESIS IMAGING (15 SHOTS) | W/Al | 31kV | 40mAs | OUT | 1.50mGy |

TOMOGRAPHIC IMAGE GENERATION DEVICE, METHOD AND RECORDING MEDIUM

CROSS-REFERENCE TO RELATED APPLICATIONS

The present application claims priority under 35 U.S.C. § 119 to Japanese Patent Application No. 2015-190658, filed on Sep. 29, 2015. The above application is hereby expressly incorporated by reference, in its entirety, into the present application.

BACKGROUND

The present disclosure relates to a tomographic image generation device, a tomographic image generation method and a tomographic image generation program for obtaining a plurality of projection images of a subject by imaging the subject with different radiation source positions, and generating a tomographic image from the projection images.

In recent years, in order to more closely observe an affected part of the body with a radiographic imaging apparatus using radiation, such as x-ray or γ-ray, tomosynthesis imaging has been proposed, in which imaging is performed by applying radiation to the subject from different radiation source positions by moving the radiation source, and a tomographic image where a desired slice plane is emphasized is generated from the thus obtained projection images. In the tomosynthesis imaging, a plurality of projection images are obtained by imaging a subject with different radiation source positions by moving the radiation source in parallel with the radiation detector or along a circular or ellipsoidal arc trajectory depending on characteristics of the imaging apparatus and necessary tomographic images, and the projection images are reconstructed to generate a tomographic image using a back projection method, such as a simple back projection method or a filtered back projection method. Generating such tomographic images for a plurality of slice planes of the subject allows separating structures overlapping with each other in the depth direction along which the slice planes are located. This in turn allows finding a lesion which is difficult to be detected in a two-dimensional image that is obtained with a conventional simple imaging method. It should be noted that the simple imaging refers to an imaging method that obtains a single two-dimensional image, which is a transmission image of the subject, by a single application of radiation to the subject.

On the other hand, the tomosynthesis imaging has a problem of blur of reconstructed tomographic images due to mechanical errors of the imaging apparatus and body motion, etc., of the subject, which is due to differences in time of imaging operations performed with different radiation source positions. When tomographic images are blurred, it is difficult to find a lesion, such as small calcifications which are useful for early detection of in particular, breast cancer when the subject is the breast. For this reason, it is commonly practiced to obtain both tomographic images and a two-dimensional image by performing the tomosynthesis imaging and the simple imaging.

For this purpose, techniques have been proposed to perform both the tomosynthesis imaging and the simple imaging using a radiographic imaging apparatus for imaging a breast (which is called "mammography") while the breast is kept compressed (see Japanese Unexamined Patent Publication No. 2007-50264 and PCT Japanese National Phase Publication No. 2012-512669, which will hereinafter be referred to as Patent Documents 1 and 2, respectively).

However, performing both the tomosynthesis imaging and the simple imaging leads to increase of the exposure dose of the subject. To address this problem, a technique has been proposed for reconstructing a tomographic image using also a two-dimensional image obtained by simple imaging, in addition to projection images (see Japanese Unexamined Patent Publication No. 2011-87917, which will hereinafter be referred to as Patent Document 3). Since a two-dimensional image allow detection of fine structures of the subject, as mentioned above, reconstructing a tomographic image using also a two-dimensional image allows improving image quality of the tomographic image. This also allows improving image quality of the tomographic image, which in turn allows reducing the amount of radiation during each imaging operation of the tomosynthesis imaging to reduce the total exposure dose of the subject.

When a radiographic image is taken, a scattered ray removing grid (which will hereinafter be simply referred to as "grid") is used to prevent lowering of the contrast due to scattered rays of the radiation in the subject. On the other hand, the tomosynthesis imaging is performed by applying radiation to the subject from different radiation source positions, and thus the incidence angle of the radiation relative to the radiation detector varies depending on the imaging position. For this reason, if the grid is used during imaging, vignetting occurs due to the radiation being blocked by the grid depending on the radiation source position, resulting in lower amounts of radiation reaching the radiation detector. Therefore the grid is not used during the tomosynthesis imaging.

Further, during the tomosynthesis imaging, imaging operations are performed with moving the radiation source, and it is necessary to perform each imaging operation with an exposure time of the subject to radiation as short as possible to prevent blur of the projection images. However, a shorter exposure time to radiation results in smaller amounts of radiation applied to the subject, and thus smaller amounts of radiation reaching the radiation detector. For this reason, during tomosynthesis imaging, high energy radiation, which is more easily transmitted through an object, is used to increase the amounts of radiation reaching the radiation detector with an exposure dose as small as possible.

SUMMARY

As described above, reconstructing a tomographic image using also a two-dimensional image obtained by simple imaging allows improving image quality of the tomographic image. The two-dimensional image is taken without using the grid, and thus has low influence of scattered rays and is a high contrast image. On the other hand, the projection images are taken without using the grid, and thus contain scattered rays, resulting in low contrast images. Further, since the projection images are taken using high energy radiation, there are small differences of radiation transmittance among tissues, and the obtained radiographic images are low contrast images. Thus, the two-dimensional image and the projection images have different image qualities, and therefore sufficient improvement of the image quality of the resulting tomographic image cannot be achieved by simply adding the two-dimensional image to the projection images to reconstruct the tomographic image.

In view of the above-described circumstances, the disclosure is directed to further improving image quality of tomographic images while achieving reduction of the exposure dose of the subject.

An aspect of a tomographic image generation device according to the disclosure comprises:

a first image obtaining unit for obtaining a plurality of first images corresponding to different radiation source positions, the first images being imaged by moving a radiation source relative to a detecting unit and applying radiation to a subject from the different radiation source positions to which the radiation source is moved under a first imaging condition for tomosynthesis imaging;

a second image obtaining unit for obtaining a second image imaged by applying the radiation to the subject from a given radiation source position under a second imaging condition for simple imaging;

an image quality correction unit for performing image quality correction on the first images to compensate for a difference of image quality between the first images and the second image based on a difference between the first imaging condition and the second imaging condition; and a reconstruction unit for reconstructing the first images having been subjected to the image quality correction and the second image to generate a tomographic image of a slice plane of the subject.

The description "moving a radiation source relative to a detecting unit" as used herein encompasses cases where only the radiation source is moved, only the detecting unit is moved, and both the radiation source and the detecting unit are moved.

The "tomosynthesis imaging" refers to an imaging method for obtaining a plurality of images corresponding to different radiation source positions by moving a radiation source relative to a detecting unit and applying radiation to the subject from the different radiation source positions to which the radiation source is moved.

The "simple imaging" refers to an imaging method for obtaining a single image by a single application of radiation to the subject.

In the tomographic image generation device according to the disclosure, the image quality correction may include at least one of scattered ray removal for removing, from the first images, scattered ray components contained in radiation transmitted through the subject when imaging under the first imaging condition is performed, and radiation quality correction for correcting for a difference of contrast between the first images and the second image due to a difference between radiation quality of the first imaging condition and radiation quality of the second imaging condition.

In this case, the image quality correction may include the scattered ray removal and the radiation quality correction.

Further, in this case, the image quality correction unit may perform the scattered ray removal before the radiation quality correction.

In the tomographic image generation device according to the disclosure, the given radiation source position may be a radiation source position where the optical axis of the radiation from the radiation source is normal to the detection unit.

In the tomographic image generation device according to the disclosure, the given radiation source position may be a radiation source position other than the different radiation source positions.

In the tomographic image generation device according to the disclosure, the different radiation source positions may include the given radiation source position.

In this case, the tomographic image generation device may further comprise a body motion determining unit for determining whether or not there is a body motion of the subject during imaging between the first image corresponding to the given radiation source position and the second image by comparing the first image corresponding to the given radiation source position with the second image, wherein, if it is determined that there is no body motion, the reconstruction unit may generate the tomographic image by reconstructing the first images having been subjected to the image quality correction, other than the first image corresponding to the given radiation source position, and the second image.

Further, in this case, if it is determined that there is a body motion, the reconstruction unit may perform, on the second image, body motion correction for correcting for positional misalignment between the subject contained in the second image and the subject contained in the first image corresponding to the given radiation source position based on the body motion, and may generate the tomographic image by reconstructing the first images having been subjected to the image quality correction, other than the first image corresponding to the given radiation source position, and the second image having been subjected to the body motion correction.

In the tomographic image generation device according to the disclosure, the first and second imaging conditions may include materials forming an anode and a filter forming the radiation source, tube voltage, and information indicating the presence or absence of a scattered ray removing grid.

In the tomographic image generation device according to the disclosure, the reconstruction unit may reconstruct the first images having been subjected to the image quality correction and the second image with assigning a larger weight to the second image than a weight assigned to the first images having been subjected to the image quality correction.

In the tomographic image generation device according to the disclosure, the reconstruction unit may comprise:

a pixel value projection unit for projecting pixel values of the first images having been subjected to the image quality correction and the second image onto coordinate positions on the slice plane of the subject based on a positional relationship between the detection unit and the radiation source position during imaging corresponding to each of the first images having been subjected to the image quality correction and the second image, while preserving the pixel values of the first images having been subjected to the image quality correction and the second image, and a pixel value calculation unit for calculating a pixel value at each coordinate position of interest based on the pixel values of the first images having been subjected to the image quality correction and the second image projected in a predetermined range relative to the coordinate position of interest on the slice plane to generate the tomographic image of the slice plane.

In this case, the pixel value calculating unit may calculate the pixel value at the coordinate position of interest by performing regression analysis on the pixel values of the first images having been subjected to the image quality correction and the second image projected on the slice plane.

The description "while preserving the pixel values of first images and the second image" as used herein refers to that the pixel values of the first images having been subjected to the image quality correction and the second image are not changed. It should be noted that, in the disclosure, the pixel value at a pixel position of any of the first images having been subjected to the image quality correction and the second image may not be able to be projected on a coordinate position on the slice plane. That is, depending on the positional relationship between the radiation source position and the detecting unit, the pixel value of the first image having been subjected to the image quality correction or the second image corresponding to a coordinate position on the slice plane may not be at a pixel position of the first image having been subjected to the image quality correction or the second image, but at a coordinate position between pixel positions of the first or second image. In such a case, the pixel value at the coordinate position on the first image having been subjected to the image quality correction or the second image to be projected on the coordinate position on the slice plane can be calculated by interpolation using pixel values at pixel positions around the coordinate position, for example. In this case, the pixel value calculated by interpolation is also a pixel value of the first image having been subjected to the image quality correction or the second image, and the pixel value of the first image having been subjected to the image quality correction or the second image calculated by interpolation is projected on the corresponding coordinate position on the slice plane while being preserved.

The "coordinate position of interest on the slice plane" as used herein refers to a coordinate position for which the pixel value is calculated to generate the tomographic image of the slice plane. The tomographic image of the slice plane can be generated by calculating the pixel value at the coordinate position of interest with sequentially changing the coordinate position of interest on the slice plane.

The "predetermined range relative to the coordinate position of interest" as used herein refers to a range of a predetermined number of coordinate positions or pixel positions around and including the pixel position of interest. For example, a range of 3×3 coordinate positions or pixel positions with the pixel position of interest being the center, or a range of 5×5 coordinate positions or pixel positions with the pixel position of interest being the center may be set as the predetermined range relative to the coordinate position of interest. It should be noted that the size of the predetermined range may be fixed or may be changed arbitrarily according to input by the operator.

The "regression analysis" is a statistical technique for analyzing a multivariate relationship. It is assumed here that observed values observed at observation points include noise added to the true values. The regression analysis is a technique to solve an inverse problem to find the true value at every observation point by regression using a least squares method, a moving average method, a kernel function, etc. In the disclosure, the pixel value at the coordinate position of interest is calculated with assuming that each coordinate position on the slice plane with the pixel values of the first images having been subjected to the image quality correction and the second image projected thereon is the observation point, each pixel value at the observation point is the observed value, and the pixel value at the coordinate position of interest is the true value.

An aspect of a tomographic image generation method according to the disclosure comprises the steps of:

obtaining a plurality of first images corresponding to different radiation source positions, the first images being imaged by moving a radiation source relative to a detecting unit and applying radiation to a subject from the different radiation source positions to which the radiation source is moved under a first imaging condition for tomosynthesis imaging;

obtaining a second image imaged by applying the radiation to the subject from a given radiation source position under a second imaging condition for simple imaging;

performing image quality correction on the first images to compensate for a difference of image quality between the first images and the second image based on a difference between the first imaging condition and the second imaging condition; and reconstructing the first images having been subjected to the image quality correction and the second image to generate a tomographic image of a slice plane of the subject.

The tomographic image generation method according to the disclosure may be provided in the form of a program for causing a computer to execute the tomographic image generation method.

According to the disclosure, the image quality correction is performed on the first images to compensate for a difference of image quality between the first images and the second image based on a difference between the first imaging condition for tomosynthesis imaging and the second imaging condition for simple imaging, and the first images having been subjected to the image quality correction and the second image are reconstructed to generate a tomographic image of a slice plane of the subject. By reconstructing a tomographic image using also the second image obtained under the second imaging condition for simple imaging in this manner, image quality of the tomographic image can be improved. Since the image quality can be improved using the second image, the radiation dose applied to the subject to obtain the first images can be reduced, thereby achieving reduction of the exposure dose of the subject. Further, since the image quality correction is performed on the first images to compensate for a difference of image quality between the first images and the second image, the image quality of the first images can be made to match the image quality of the second image, or the image quality of the first images can be made to be similar to the image quality of the second image to reduce the difference between the image quality of first images and the image quality of the second image. Thus, higher image quality of the tomographic image can be achieved, and further reduction of the exposure dose of the subject can be achieved.

BRIEF DESCRIPTION OF THE DRAWINGS

FIG. 20 shows a table for explaining exposure dose.

DETAILED DESCRIPTION OF THE PREFERRED EMBODIMENTS

Figure 1:
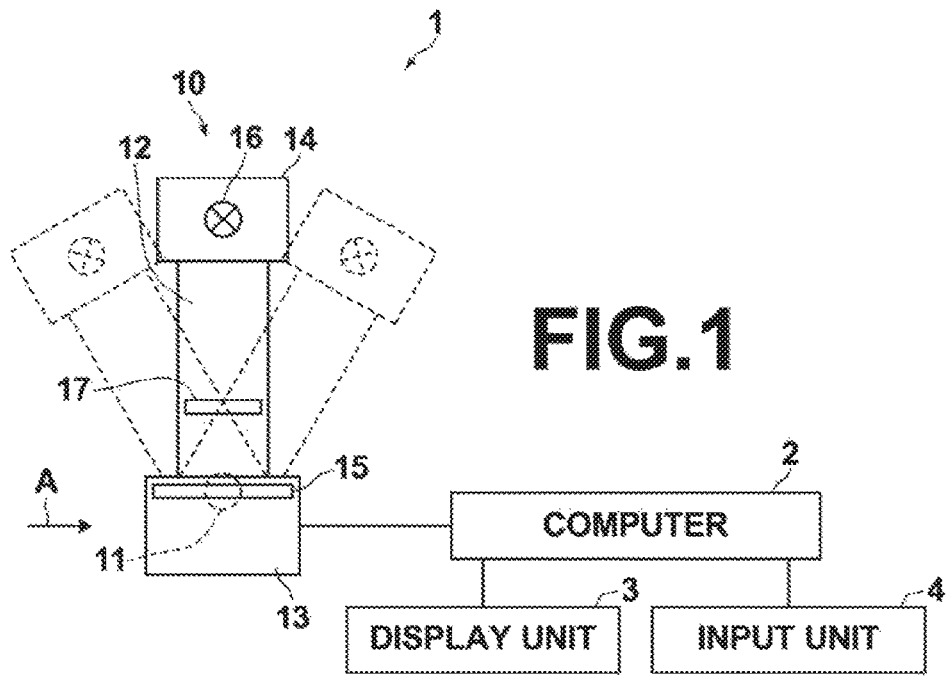
FIG. 1 is a diagram illustrating the schematic configuration of a radiographic imaging apparatus to which a tomographic image generation device according to a first embodiment of the disclosure is applied.
Figure 2:
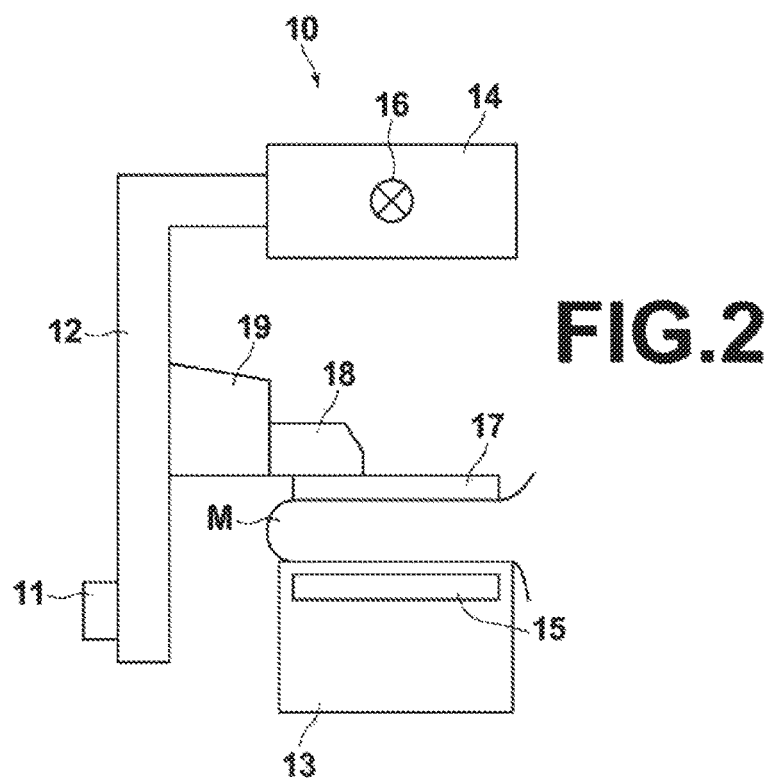
FIG. 2 is a diagram illustrating the radiographic imaging apparatus viewed from the direction of arrow A in FIG. 1.

Hereinafter, embodiments of the present disclosure will be described with reference to the drawings. FIG. 1 is a diagram illustrating the schematic configuration of a radiographic imaging apparatus to which a tomographic image generation device according to a first embodiment of the disclosure is applied, and FIG. 2 is a diagram illustrating the radiographic imaging apparatus viewed from the direction of arrow A in FIG. 1. The radiographic imaging apparatus 1 is a mammographic imaging apparatus that images a breast M, which is the subject, with different radiation source positions, which correspond to different imaging directions, to obtain a plurality of radiographic images, i.e., projection images, to generate a tomographic image of the breast by performing tomosynthesis imaging. As shown in FIG. 1, the radiographic imaging apparatus 1 includes an imaging unit 10, a computer 2 connected to the imaging unit 10, and a display unit 3 and an input unit 4 connected to the computer 2. It should be noted that the radiographic imaging apparatus 1 according to this embodiment also obtains a two-dimensional image, which is a transmission image of the breast M, by performing simple imaging, as described later. The projection images correspond to first images, and the two-dimensional image corresponds to a second image.

The imaging unit 10 includes an arm 12, which is coupled to a base (not shown) via a rotatable shaft 11. An imaging table 13 is attached to one end of the arm 12, and a radiation applying unit 14 is attached to the other end of the arm 12 so as to face the imaging table 13. The arm 12 is configured such that only the end to which the radiation applying unit 14 is attached can be rotated, thereby allowing only the radiation applying unit 14 to be rotated while the imaging table 13 is fixed. Rotation of the arm 12 is controlled by the computer 2.

The imaging table 13 includes therein a radiation detector 15, such as a flat panel detector. The imaging table 13 also includes therein a circuit board, etc., which includes a charge amplifier for converting an electric charge signal read out from the radiation detector 15 into a voltage signal, a correlated double sampling circuit for sampling the voltage signal outputted from the charge amplifier, and an AD converter for converting the voltage signal into a digital signal, etc. It should be noted that the radiation detector 15 corresponds to a detection unit.

The radiation detector 15 is of a type that is repeatedly usable to record and read out a radiographic image on and from it. The radiation detector 15 may be a so-called direct-type radiation detector, which directly receives the radiation and generates electric charges, or may be a so-called indirect-type radiation detector, which once converts the radiation into visible light, and then converts the visible light into electric charge signals. As the reading system to read out the radiographic image signal, it is desirable to use a so-called TFT reading system, which reads out the radiographic image signal with turning on and off TFT (thin film transistor) switches, or a so-called optical reading system, which reads out the radiographic image signal by applying reading light. However, this is not intended to limit the invention and any other reading system may be used.

The radiation applying unit 14 contains therein an x-ray source 16, which is a radiation source. Timing of application of x-rays, or radiation, from the x-ray source 16 and x-ray generation conditions for the x-ray source 16, i.e., materials forming an anode and a filter, tube voltage, and exposure time, etc., are controlled by the computer 2.

To the arm 12, a compression paddle 17 disposed above the imaging table 13 for compressing the breast M, a support 18 for supporting the compression paddle 17, and a moving mechanism 19 for moving the support 18 in the vertical direction, as shown in FIGS. 1 and 2, are attached. It should be noted that the spacing between the compression paddle 17 and the imaging table 13, i.e., compression thickness, is inputted to the computer 2.

The display unit 3 is a display device, such as a CRT or a liquid crystal monitor. The display unit 3 displays projection images and a two-dimensional image which are obtained as described later, a generated tomographic image, and messages necessary for operation, etc. The display unit 3 may include a built-in speaker for outputting sound.

The input unit 4 is formed by a keyboard, a mouse, and/or a touch-panel input device. The input unit 4 receives operation by the operator of the radiographic imaging apparatus 1. The input unit 4 also receives input of various information, such as imaging conditions, necessary for performing tomosynthesis imaging, and instructions to modify the information. In this embodiment, the individual units of the radiographic imaging apparatus 1 operate according to the information inputted by the operator via the input unit 4.

A tomographic image generation program is installed on the computer 2. In this embodiment, the computer may be a work station or a personal computer which is directly operated by the operator, or may be a server computer connected to the work station or the personal computer via a network. The tomographic image generation program is distributed with being recorded on a recording medium, such as a DVD (Digital Versatile Disc) or a CD-ROM (Compact Disc Read Only Memory), and is installed on the computer from the recording medium. Alternatively, the tomographic image generation program is stored on a storage device of a server computer connected to a network or a network storage such that it is externally accessible, and is download and installed on the computer in response to a request.

Figure 3:
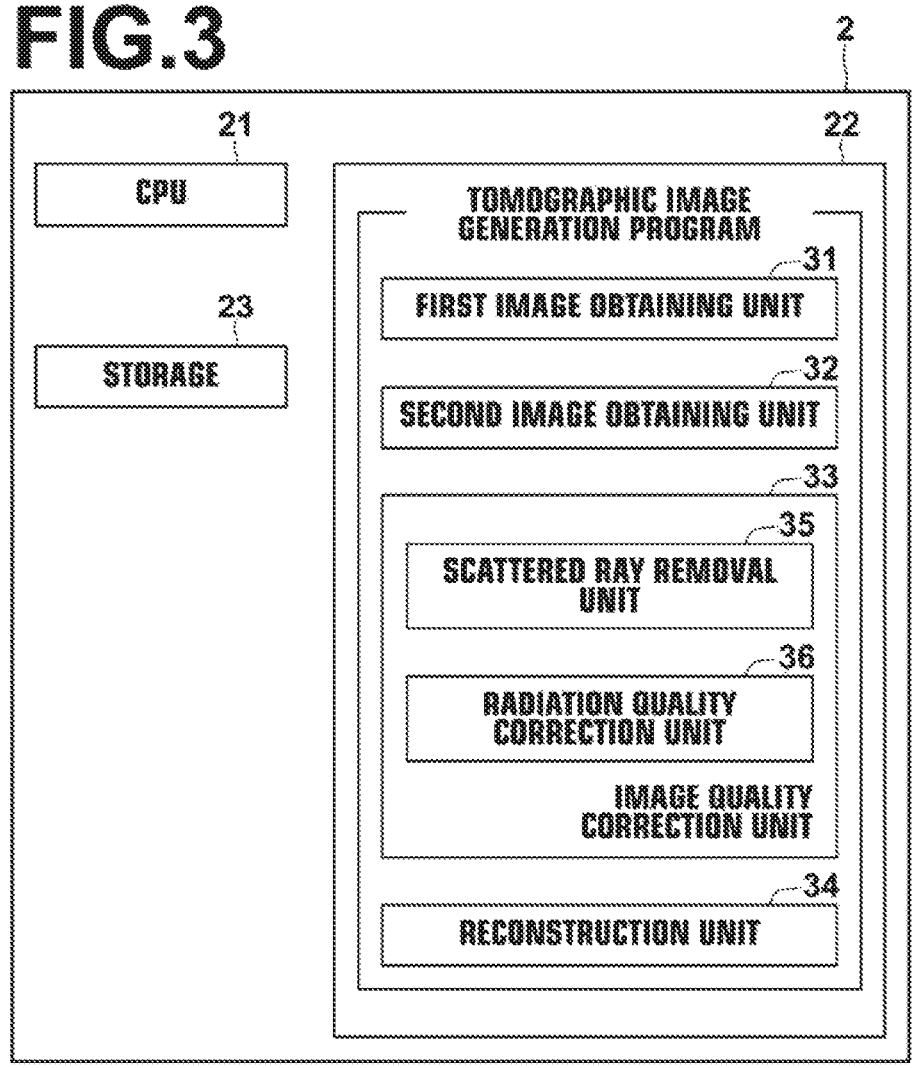
FIG. 3 is a diagram illustrating the schematic configuration of the tomographic image generation device of the first embodiment implemented by installing a tomographic image generation program on a computer.

FIG. 3 is a diagram illustrating the schematic configuration of the tomographic image generation device implemented by installing the tomographic image generation program on the computer 2. As shown in FIG. 3, the tomographic image generation device includes a CPU (Central Processing Unit) 21, a memory 22, and a storage 23, as the configuration of a standard computer.

The storage 23 is formed by a storage device, such as a hard disk or SSD (solid state drive). The storage 23 stores various information including programs for driving the individual units of the radiographic imaging apparatus 1, and the tomographic image generation program. The storage 23 also stores projection images obtained by tomosynthesis imaging, a two-dimensional image obtained by simple imaging, and a tomographic image which is generated as described later. The storage 23 also stores various tables, which will be described later.

The memory 22 temporarily stores the programs stored in the storage 23 for the CPU 21 to execute various operations. The tomographic image generation program defines, as the operations to be executed by the CPU 21: a first image obtaining operation for obtaining a plurality of projection images of the breast M corresponding to different radiation source positions by causing the radiographic imaging apparatus 1 to perform tomosynthesis imaging under a first imaging condition for tomosynthesis imaging; a second image obtaining operation for obtaining a two-dimensional image imaged by applying radiation to the breast M under a second imaging condition for simple imaging from a given radiation source position; an image quality correction operation for performing image quality correction on the projection images to compensate for a difference of image quality between the projection images and the two-dimensional image based on a difference between the first imaging condition and the second imaging condition; and a reconstruction operation for generating a tomographic image of a slice plane of the breast M by reconstructing the projection images having been subjected to the image quality correction operation and the two-dimensional image.

When the CPU 21 executes the above-described operations according to the tomographic image generation program, the computer 2 functions as a first image obtaining unit 31, a second image obtaining unit 32, an image quality correction unit 33, and a reconstruction unit 34. It should be noted that the computer 2 may include processors for executing the first image obtaining operation, the second image obtaining operation, the image quality correction, and the reconstruction operation, respectively.

Figure 4:
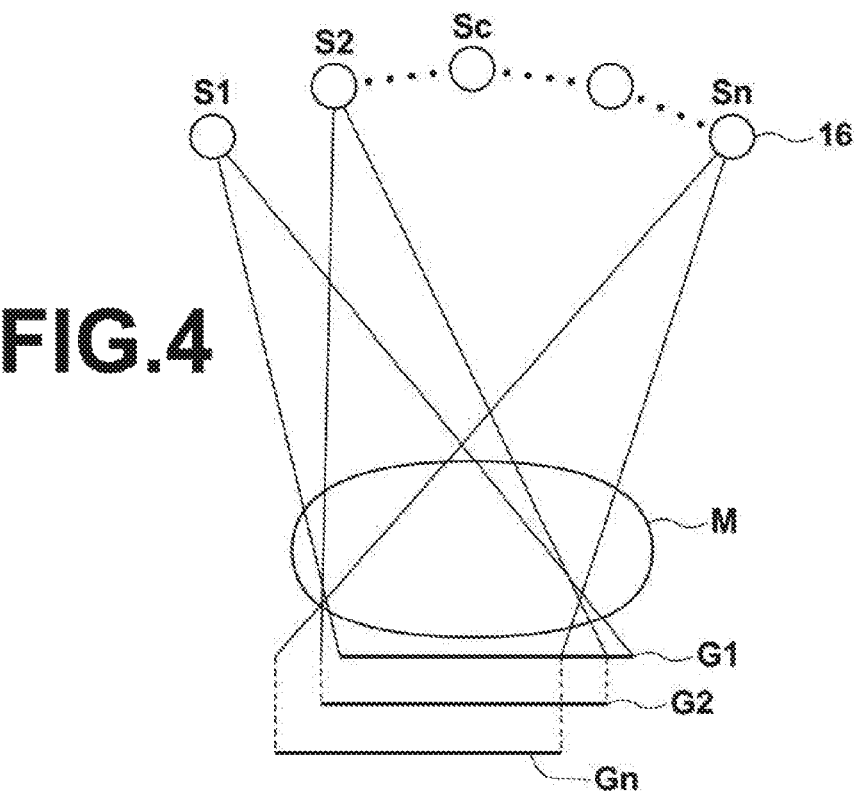
FIG. 4 is a diagram for explaining how projection images are obtained.

The first image obtaining unit 31 causes the arm 12 to rotate about the rotatable shaft 11 to move the x-ray source 16, applies x-rays to the breast M, which is the subject, from different radiation source positions to which the x-ray source 16 is moved under the first imaging condition for tomosynthesis imaging, and detects the x-rays transmitted through the breast M with the radiation detector 15 to obtain a plurality of projection images Gi (i=1 to n, where n is the number of radiation source positions) corresponding to the different radiation source positions. FIG. 4 is a diagram for explaining how the projection images Gi are obtained. As shown in FIG. 4, the x-ray source 16 is moved to each of radiation source positions S1, S2, . . . , Sn, and the x-ray source 16 is activated at each radiation source position to apply x-rays to the breast M. Then, the x-rays transmitted through the breast M are detected with the radiation detector 15 to obtain projection images G1, G2, . . . , Gn corresponding to the radiation source positions S1 to Sn. It should be noted that, from each of the radiation source positions S1 to Sn, x-rays of the same radiation dose are applied to the breast M. The obtained projection images Gi are stored in the storage 23. It should be noted that the projection images Gi may be obtained and stored in the storage 23 under the control of a program separate from the tomographic image generation program. In this case, the first image obtaining unit 31 reads out the projection images Gi, which are stored in the storage 23, from the storage 23 for the image quality correction operation and the reconstruction operation.

In this embodiment, imaging is not performed with a radiation source position Sc where the optical axis of x-rays from the x-ray source 16 is normal to the radiation detector 15. Therefore, a projection image corresponding to the radiation source position Sc is not obtained, and therefore the number of projection images is n−1. It should be noted that the radiation source position Sc corresponds to the given radiation source position.

Figure 5:
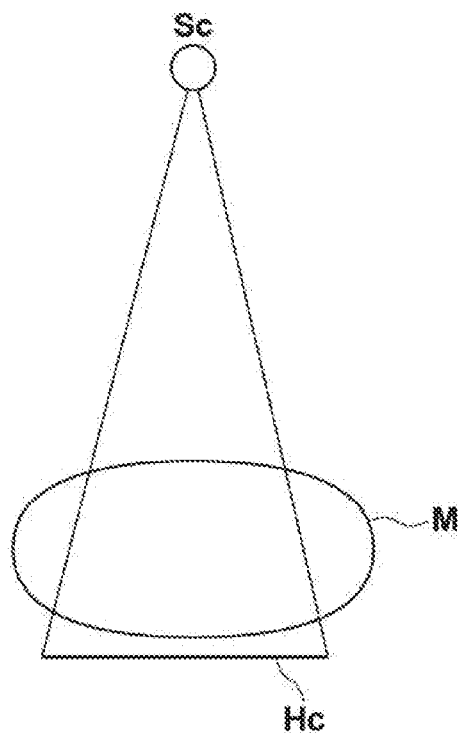
FIG. 5 is a diagram for explaining how a two-dimensional image is obtained.
Figures 6, 7:
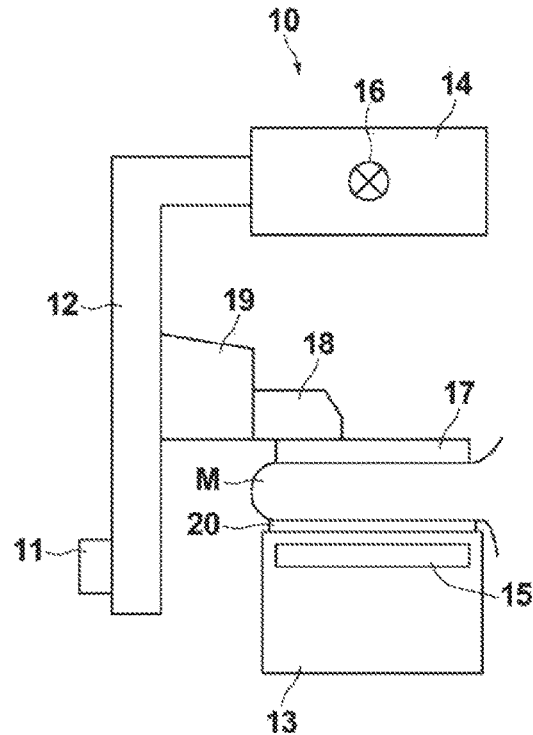
FIG. 6 is a diagram showing the radiographic imaging apparatus viewed in the direction of arrow A in FIG. 1 during imaging to obtain the two-dimensional image.
FIG. 7 shows a table of imaging conditions.

The second image obtaining unit 32 obtains a two-dimensional image Hc. FIG. 5 is a diagram for explaining how the two-dimensional image Hc is obtained. As shown in FIG. 5, the second image obtaining unit 32 obtains the two-dimensional image Hc, which is a two-dimensional radiographic image, by rotating the arm 12 about the rotatable shaft 11 to move the x-ray source 16 to the radiation source position Sc, applying x-rays to the breast M, which is the subject, from the radiation source position Sc under the second imaging condition for simple imaging, and detecting the x-rays transmitted through the breast M with the radiation detector 15. It should be noted that, during the simple imaging, a scattered ray removing grid 20 (which will hereinafter simply be referred to as "grid") is disposed between the breast M and the radiation detector 15, as shown in FIG. 6, to remove scattered rays transmitted through the breast M. During the tomosynthesis imaging, the grid 20 is not disposed, as shown in FIG. 2. It should be noted that when the grid 20 is disposed, the compression thickness is the spacing between the upper surface of the grid 20 and the compression paddle 17.

Now, the first and second imaging conditions are described. The x-ray source 16 includes a filament for emitting electron beams, a target for generating x-rays when it is hit by the electron beams, and a filter for adjusting the energy spectrum of the x-rays. The target includes a plurality of different anode materials, such as Mo, Rh, and W, which are disposed in a selectable manner. The filter includes a plurality of different materials, such as Mo, Rh, W, and Al, which are disposed in a selectable manner.

The imaging conditions are conditions for adjusting the energy spectrum (radiation quality) of the x-rays applied to the breast M to obtain appropriate radiographic images, and includes, for example, the types of the target and the filter forming the x-ray source 16, an x-ray generation condition including a tube voltage applied between the filament and the target, and a grid condition indication the presence or absence of the grid 20. It should be noted that the imaging conditions may include a mAs value (tube current×radiation exposure time). Further, when the grid is used, the type of the grid, i.e., the grid ratio, the grid density, whether the grid is of a converging type or a parallel type, the convergence distance when the grid is of a converging type, and the material for providing an interspacing (aluminum, fiber, bakelite, etc.), etc., influence the grid characteristics, which will be described later. For this reason, the imaging conditions include grid information indicating the type of the grid.

In this embodiment, tables containing the imaging conditions for tomosynthesis imaging and simple imaging, respectively, are stored in the storage 23. FIG. 7 shows a table of imaging conditions. As shown in FIG. 7, a table LUT1 of imaging conditions defines imaging conditions corresponding to different breast thicknesses. Specifically, T/F indicating the types of the target and the filter, the tube voltage, and the presence or absence of the grid are set. It should be noted that IN indicates that the grid is present, and OUT indicates that the grid is absent. Referencing the table LUT1, when the breast thickness is 45 mm, for example, the T/F being W/Al (which means that the target is W and the filter is Al), the tube voltage being 32 kV, and the grid being absent are set as the first imaging condition for tomosynthesis imaging. For the simple imaging, the T/F being W/Rh (which means that the target is W and the filter is Rh), the tube voltage being 29 kV, and the grid being present are set as the second imaging condition. The set first and second imaging conditions are stored in the storage 23.

Figure 8:
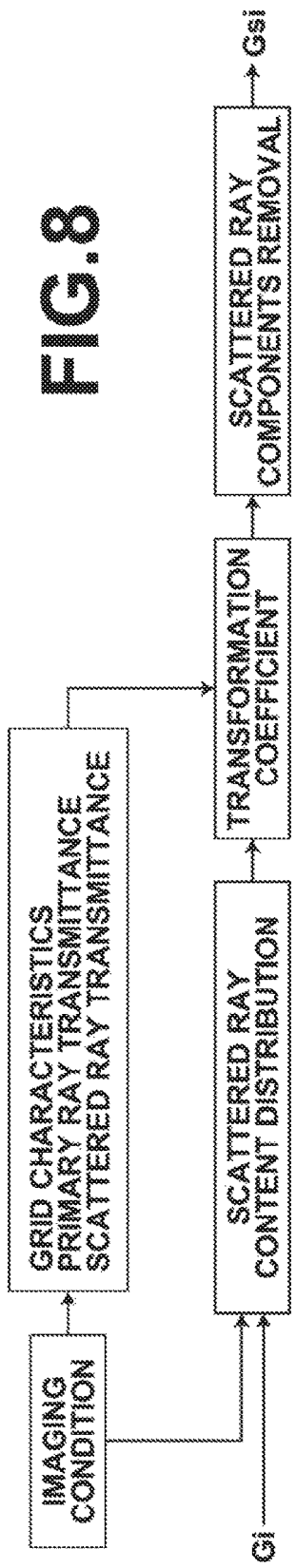
FIG. 8 is a block diagram for explaining scattered ray removal.

The image quality correction unit 33 includes a scattered ray removal unit 35 and a radiation quality correction unit 36. During the tomosynthesis imaging under the first imaging condition, the scattered ray removal unit 35 performs, on the projection images Gi (other than a projection image corresponding to the radiation source position Sc; the same applies in the following description), scattered ray removal for removing scattered ray components contained in the x-rays transmitted through the breast M from the projection images Gi. In this embodiment, the technique disclosed in Japanese Unexamined Patent Publication Nos. 2014-207958 and 2015-089429, for example, is used to achieve the scattered ray removal. Now, the scattered ray removal operation is described. FIG. 8 is a block diagram showing the scattered ray removal operation.

First, the scattered ray removal unit 35 obtains grid characteristics from the grid information contained in the second imaging condition stored in the storage 23. The grid characteristics include a scattered ray transmittance Ts of the grid 20 used during the simple imaging, and a transmittance of primary rays (primary ray transmittance) Tp transmitted through the breast M and applied to the radiation detector 15 without being scattered. It should be noted that, in this embodiment, a table associating the grid information with the grid characteristics is stored in the storage 23, and the scattered ray removal unit 35 references this table to obtain the grid characteristics based on the grid information.

Further, the scattered ray removal unit 35 calculates a primary ray image and a scattered ray image from a subject thickness distribution T(x, y) of the subject captured in the projection images Gi based on the equations (1) and (2) below, and calculates a scattered ray content distribution S(x, y) from the calculated primary ray image and scattered ray image based on the equation (3) below:

$$Icp(x,y)=Io(x,y)\times\exp(-\mu\times T(x,y)) \quad (1),$$

$$Ics(x,y)=Io(x,y)*S\sigma(T(x,y)) \quad (2),$$

and $$S(x,y)=Ics(x,y)/(Ics(x,y)+Icp(x,y)) \quad (3),$$

where (x, y) is coordinates of each pixel position of the projection images Gi, Icp(x, y) is a primary ray image at the pixel position (x, y), Ics(x, y) is a scattered ray image at the pixel position (x, y), Io(x, y) is an incident radiation dose on the surface of the subject at the pixel position (x, y), $\mu$ is a linear attenuation coefficient of the breast M, which is the subject, and $S\sigma(T(x, y))$ is a convolution kernel function representing characteristics of scattering depending on the subject thickness at the pixel position (x, y). It should be noted that, in this embodiment, the compression thickness during the tomosynthesis imaging may be used as the subject thickness distribution T(x, y). The compression thickness is constant in the area of the breast M contained in the projection image Gi. Thus, in this embodiment, the scattered ray content distribution S(x, y) can be calculated with a relatively low amount of calculation. The symbol "*" in the equation (2) is an operator representing a convolution calculation. Further, $S\sigma(T(x, y))$ can be found experimentally depending on the imaging conditions. In this embodiment, a table associating various imaging conditions with vales of $S\sigma(T(x, y))$ is stored in the storage 23 to find the value of $S\sigma(T(x, y))$ by referencing this table based on the first imaging condition.

Then, the scattered ray removal unit 35 calculates a transformation coefficient R(x, y) for transforming the projection images Gi according to the equation (4) below, based on the scattered ray transmittance Ts, the primary ray transmittance Tp, and the scattered ray content distribution S(x, y), which are the grid characteristics. Further, the scattered ray removal unit 35 removes the scattered ray components from the projection images Gi by multiplying the pixel value of each pixel of the projection images Gi with the transformation coefficient R(x, y) according to the equation (5) below to obtain projection images Gsi having been subjected to the scattered ray removal.

$$R(x,y)=S(x,y)\times Ts+(1-S(x,y))\times Tp \quad (4),$$

$$Gs(x,y)=R(x,y)\times G(x,y) \quad (5)$$

It should be noted that each projection image Gi may be decomposed into a plurality of frequency bands, and the calculation of the transformation coefficient and the multiplication of the transformation coefficient may be performed for each frequency band. In this case, frequency synthesis is performed on projection images of the individual frequency bands multiplied with the transformation coefficient to obtain the projection images Gsi having been subjected to the scattered ray removal.

The radiation quality correction unit 36 performs radiation quality correction for correcting for a difference of contrast between the projection images Gi and the two-dimensional image Hc due to a difference between the radiation quality of the first imaging condition and the radiation quality of the second imaging condition. It should be noted that the radiation quality correction is performed on the projection images Gsi having been subjected to the scattered ray removal. The radiation quality correction is achieved using the technique described in Japanese Unexamined Patent Publication No. 2014-014655, for example. Now, the radiation quality correction operation is described. First, the radiation quality correction unit 36 obtains first contrast information indicating the contrast of the projection images Gi. In this embodiment, for each combination of the target and the filter used during imaging, a contrast table, which is a three-dimensional table defining contrast values corresponding to different thicknesses of the breast M and different tube voltages is stored. The radiation quality correction unit 36 references the contrast table to obtain the first contrast information indicating the contrast of the projection images Gi based on the first imaging condition and the thickness of the breast M.

Figures 9, 10:
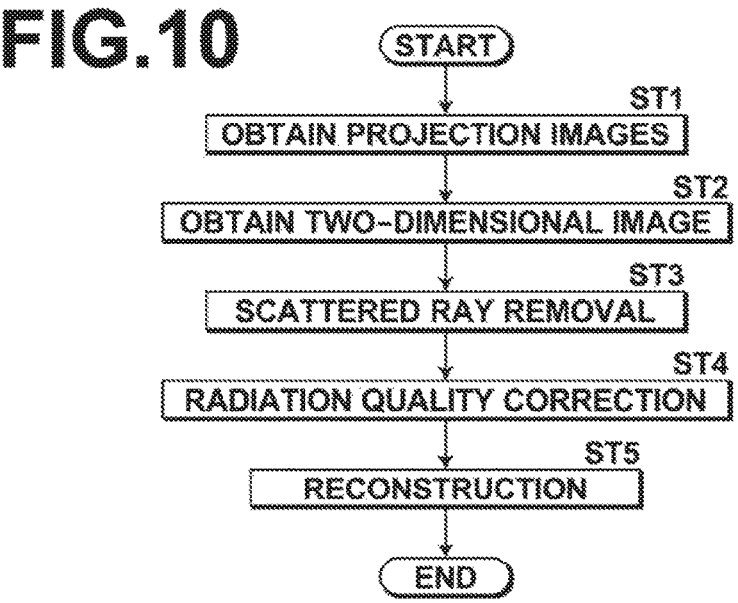
FIG. 9 shows a contrast table.
FIG. 10 is a flow chart showing the process performed in the first embodiment.

FIG. 9 shows a contrast table, which is a table defining the contrast information. As shown in FIG. 9, a contrast table LUT2 is a three-dimensional table defining, for each combination of the target and the filter, contrast values corresponding to different thicknesses of the breast M, different tube voltages, and different mammary gland/fat ratios. It should be noted that the contrast table LUT2 shown in FIG. 9 defines contrast values corresponding to different thicknesses of the breast and different tube voltages when the combination of the target and the filter is W/Rh, and the mammary gland/fat ratio is 50%. It should be noted that, while the contrast table LUT2 is shown as a two-dimensional table in FIG. 9, it is actually a three-dimensional table that defines two-dimensional tables, as shown in FIG. 9, corresponding to different mammary gland/fat ratios. Further, in the contrast table LUT2, the thicknesses of the breast are discretely defined with an interval of 20 mm, the tube voltages are discretely defined with an interval of 2 kV, and the mammary gland/fat ratios are discretely defined with an interval of 10%, for example, as shown in FIG. 9 for example. A contrast value corresponding to a breast thickness, a tube voltage, and a mammary gland/fat ratio that are not defined in the contrast table LUT2 may be calculated by interpolation using contrast values corresponding to neighboring breast thicknesses, tube voltages, and mammary gland/fat ratios defined in the contrast table LUT2.

It should be noted that the contrast values defined in the contrast table are calculated by simulation. In this embodiment, a difference between a signal value at mammary glands and a signal value at fat contained in the breast M in a radiographic image is defined as a contrast value. Actually, the mammary glands and the fat are contained in radiographic images with being superimposed one on the other. In this embodiment, a difference between a signal value of a radiographic image when it is assumed that the mammary glands are present in a ratio of 50% (i.e., the mammary gland/fat ratio is 50%) and a signal value of a radiographic image when it is assumed that the mammary glands of a thickness of 5 mm are present in a ratio of 100% (i.e., the mammary gland/fat ratio is 100%) within the background where the mammary gland/fat ratio is 50% is defined as a contrast value. Specifically, assuming a subject having a given thickness to be defined in the contrast table, it is assumed that tissues of 100% mammary glands (mammary gland tissues) of a thickness of 5 mm are present inside the subject. It should be noted that, with respect to background tissues other than the mammary gland tissues, it is assumed that the mammary glands are present in a ratio of 50%. Then, a signal value QA obtained from x-rays transmitted through the mammary gland tissues and a signal value QB obtained from x-rays transmitted only through the background tissues are calculated, and log(QB)−log(QA) is calculates as a contrast value.

Further, the radiation quality correction unit 36 obtains second contrast information indicating a contrast value of the two-dimensional image Hc. The second contrast information is also calculated by referencing the above-described contrast table based on the second imaging condition and the thickness of the breast M.

Then, the radiation quality correction unit 36 determines the amount of correction for the contrast of the projection images Gsi based on the first contrast information and the second contrast information. Assuming that the first contrast is A and the second contrast is B, the amount of correction is calculated as B/A. Further, the radiation quality correction unit 36 performs tone processing on the projection images Gsi based on the determined amount of contrast correction to obtain processed projection images Gsfi having been subjected to the image quality correction. In this operation, the radiation quality correction unit 36 first corrects a tone processing condition, which is the base of the tone correction, based on the determined amount of contrast correction.

For example, if the amount of contrast correction is 1.35, the inclination of a tone curve representing the tone processing condition is increased 1.35 times. Then, the radiation quality correction unit 36 performs the tone processing on the radiographic images using the corrected tone processing condition to obtain the processed projection images Gsfi. It should be noted that the image quality correction unit 33 may further analyze the projection images Gsfi, set image processing conditions including a normalization condition, an edge emphasis condition, a frequency processing condition, a noise filtering condition, a dynamic range adjustment condition, and a tone processing condition, and further preform image processing based on the image processing conditions set for the projection images Gsfi. Further, the two-dimensional image Hc may be subjected to image processing other than the scattered ray removal and the radiation quality correction.

The reconstruction unit 34 reconstructs the processed projection images Gsfi and the two-dimensional image Hc to generate a tomographic image where a desired slice plane of the breast M is emphasized. Specifically, the reconstruction unit 34 reconstructs the projection images Gsfi and the two-dimensional image Hc by using a known back projection method, such as simple back projection or filtered back projection, to generate a tomographic image of each of different slice planes. At this time, the two-dimensional image Hc is used for the reconstruction in place of a projection image corresponding to the radiation source position Sc. It should be noted that, during the reconstruction, a weight may be assigned to the two-dimensional image Hc. The weight is assigned such that a larger weight is assigned to the two-dimensional image Hc than those assigned to the projection images Gsfi.

Next, the process performed in the first embodiment is described. FIG. 10 is a flow chart showing the process performed in the first embodiment. When the input unit 4 has received an instruction to start the process inputted by the operator, the tomosynthesis imaging is performed under the first imaging condition, and the first image obtaining unit 31 obtains a plurality of projection images Gi (step ST1). Then, the x-ray source 16 is moved to the radiation source position Sc and the simple imaging is performed under the second imaging condition, and the second image obtaining unit 32 obtains a two-dimensional image Hc (step ST2). It should be noted that the two-dimensional image Hc may be obtained first.

Subsequently, the scattered ray removal unit 35 of the image quality correction unit 33 performs the scattered ray removal to remove scattered ray components contained in x-rays transmitted through the breast M during the tomosynthesis imaging from the projection images Gi (step ST3) Further, the radiation quality correction unit 36 of the image quality correction unit 33 performs, on the projection images Gsi having been subjected to the scattered ray removal, the radiation quality correction to correct for a difference of contrast between the projection images Gi and the two-dimensional image Hc due to a difference between the radiation quality of the first imaging condition and the radiation quality of the second imaging condition (step ST4) to obtain processed projection images Gsfi.

Then, the reconstruction unit 34 reconstructs the processed projection images Gsfi and the two-dimensional image Hc to generate a tomographic image of each of different slice planes of the breast M (step ST5), and the process ends.

As described above, in the first embodiment, the image quality correction is performed on the projection images Gi to compensate for a difference of image quality between the projection images Gi and the two-dimensional image Hc based on a difference between the first imaging condition for tomosynthesis imaging and the second imaging condition for simple imaging, and the projection images Gsfi having been subjected to the image quality correction and the two-dimensional image Hc are reconstructed to generating a tomographic image of a slice plane of the breast M. By reconstructing a tomographic image using the two-dimensional image Hc obtained under the second imaging condition for simple imaging in this manner, image quality of the tomographic images can be improved. Since the image quality can be improved using the two-dimensional image Hc, an x-ray dose applied to the breast M to obtain the projection images Gi can be reduced, thereby achieving reduction of the exposure dose of the subject. Further, since the image quality correction is performed on the projection images Gi to compensate for a difference of image quality between projection images Gi and the two-dimensional image Hc, the image quality of the projection images Gi can be made to match the image quality of the two-dimensional image Hc, or the image quality of the projection images Gi can be made to be similar to the image quality of the two-dimensional image Hc to reduce the difference between the image quality of the projection images Gi and the image quality of the two-dimensional image Hc. Thus, higher image quality of the tomographic images can be achieved, and further reduction of the exposure dose of the breast M, which is the subject, can be achieved.

Further, performing the scattered ray removal on the projection images Gi allows removing the scattered ray components from the projection images Gi. Performing the radiation quality correction allows making the contrast of the projection images Gsi match the contrast of the two-dimensional image Hc. Thus, higher image quality of the tomographic images can be achieved without being influenced by blur due to the scattered rays and the low contrast of the images.

The scattered rays during imaging occur in different manners depending on the radiation quality of x-rays. In the case where the image quality correction includes the scattered ray removal and the radiation quality correction, if the radiation quality correction is performed first, the radiation quality correction has to be performed with taking the extent of scattered rays that occur depending on the radiation quality into account. It is, however, technically difficult to perform the radiation quality correction with taking the extent of scattered rays that occur depending on the radiation quality into account. For this reason, the image quality correction can be facilitated by performing the scattered ray removal before the radiation quality correction.

Further, in the case where the projection images Gsfi and the two-dimensional image Hc are reconstructed with assigning a larger weight to the two-dimensional image Hc than those assigned to the projection images Gsfi, the reconstruction with higher influence of the two-dimensional image Hc, which has higher image quality, can be achieved. This allows achieving higher image quality of the tomographic image and further reduction of the exposure dose of the subject.

Figure 11:
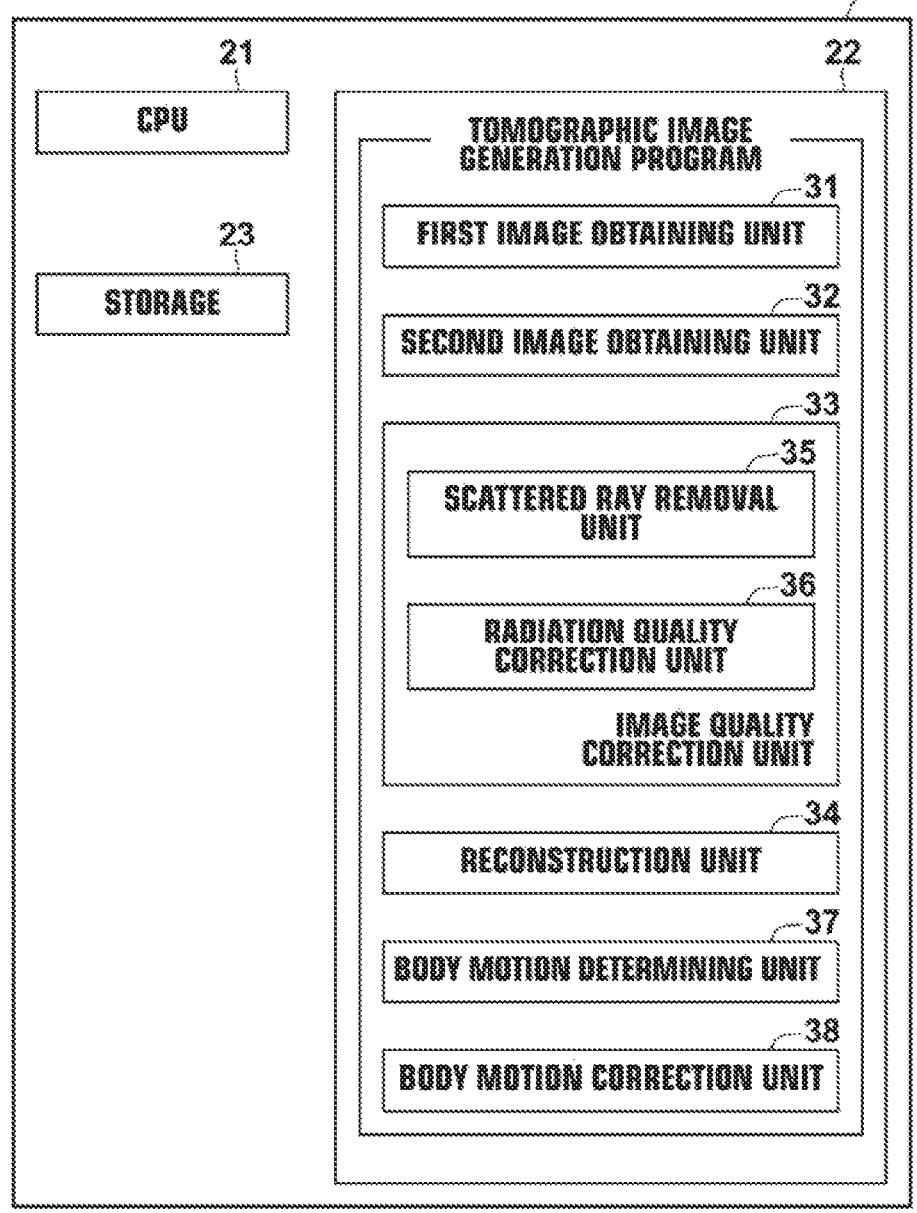
FIG. 11 is a diagram illustrating the schematic configuration of a tomographic image generation device of a second embodiment implemented by installing a tomographic image generation program on a computer.

Next, a second embodiment of the disclosure is described. FIG. 11 shows the schematic configuration of a radiographic imaging apparatus to which a tomographic image generation device according to the second embodiment of the disclosure is applied. It should be noted that features of the second embodiment that are the same as those in the first embodiment are assigned with the same reference numerals, and are not described in detail. As shown in FIG. 11, the difference between the second embodiment and the first embodiment lies in that the radiographic imaging apparatus 1 according to the second embodiment also obtains a projection image Gc corresponding to the radiation source position Sc by performing the tomosynthesis imaging with the radiation source position Sc, and includes a body motion determining unit 37 for determining whether or not there is a body motion of the breast M during imaging between the projection image Gc corresponding to the radiation source position Sc and the two-dimensional image Hc corresponding to the radiation source position Sc by comparing the projection image Gc with the two-dimensional image Hc, and a body motion correction unit 38 for performing a body motion correction operation on the two-dimensional image Hc, as necessary, wherein the reconstruction unit 34 performs the reconstruction depending on whether or not there is a body motion.

Figure 12:
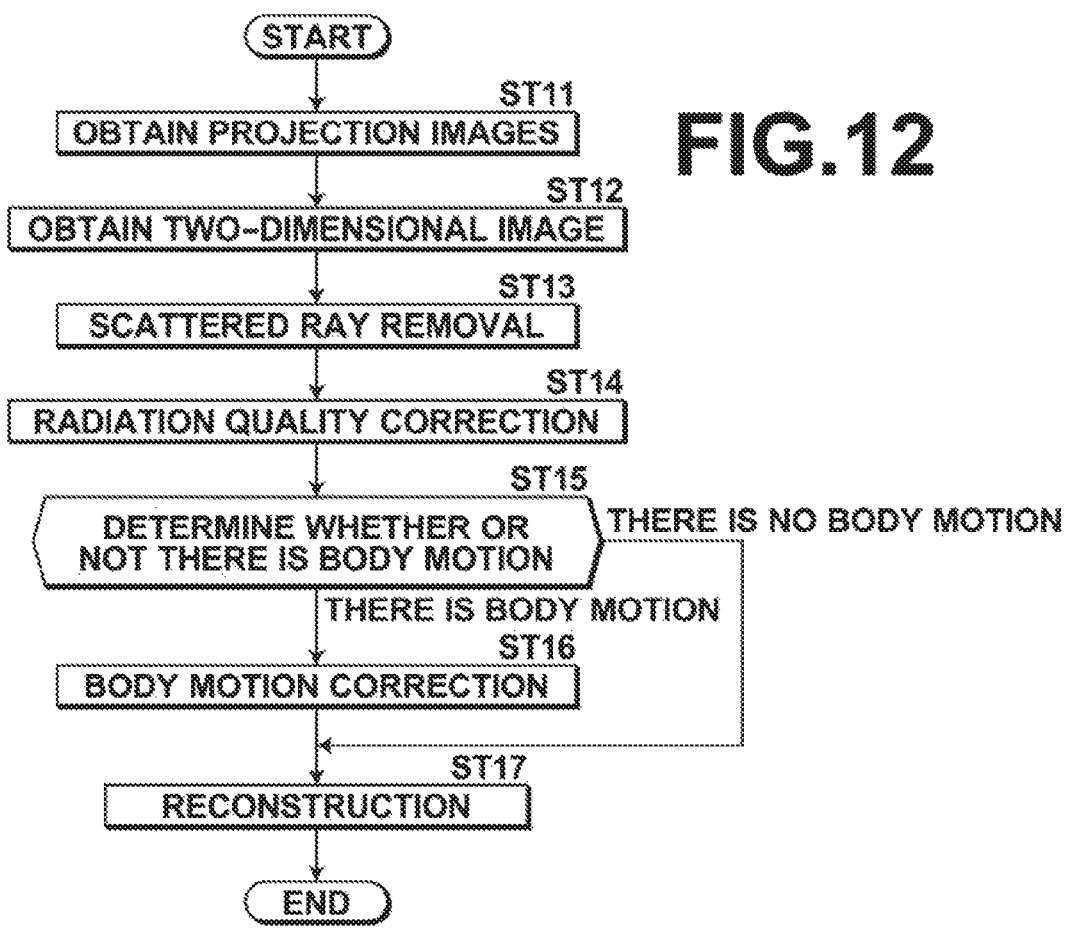
FIG. 12 is a flow chart showing the process performed in the second embodiment.

Next, the process performed in the second embodiment is described. FIG. 12 is a flow chart showing the process performed in the second embodiment. When the input unit 4 has received an instruction to start the process inputted by the operator, the tomosynthesis imaging is performed under the first imaging condition and the first image obtaining unit 31 obtains a plurality of projection images Gi (step ST11). It should be noted that, in the second embodiment, this imaging is also performed with the radiation source position Sc to obtain a projection image Gc. Then, the x-ray source 16 is moved to the radiation source position Sc to perform the simple imaging under the second imaging condition, and the second image obtaining unit 32 obtain a two-dimensional image Hc (step ST12).

Subsequently, similarly to the operations in steps ST3 and ST4, the scattered ray removal unit 35 of the image quality correction unit 33 performs the scattered ray removal on the projection images Gi (step ST13) Further, the radiation quality correction unit 36 of the image quality correction unit 33 performs the radiation quality correction on projection images Gsi having been subjected to the scattered ray removal (step ST14) to obtain processed projection images Gsfi.

Then, the body motion determining unit 37 compares the projection image Gc corresponding to the radiation source position Sc with the two-dimensional image Hc to determine whether or not there is a body motion of the breast M during imaging between the projection image Gc corresponding to the radiation source position Sc and the two-dimensional image Hc (step ST15). Specifically, the body motion determining unit 37 calculates a normalized cross-correlation value for each local area of the projection image Gc and the two-dimensional image Hc, and if the normalized cross-correlation value is not greater than a predetermined threshold value Th1, the body motion determining unit 37 determines that there is a body motion. It should be noted that the local areas are set such that they cover the entire area of the breast M captured in the projection image Gc and the two-dimensional image Hc. The projection image Gc may be one before the image quality correction or after the image quality correction.

When it is determined by the body motion determining unit 37 that there is a body motion, the body motion correction unit 38 performs body motion correction on the two-dimensional image Hc (step ST16). Specifically, the body motion correction unit 38 calculates a local motion vector that indicates the amount and the direction of movement of the two-dimensional image Hc relative to the projection image Gc for each local area. Then, the body motion correction is performed on the two-dimensional image Hc by translating, rotating, and/or enlarging or reducing the two-dimensional image Hc for each local area.

Then, the reconstruction unit 34 reconstructs the two-dimensional image Hc having been subjected to the body motion correction and the processed projection images Gsfi other than the projection image Gc to generate a tomographic image of each of different slice planes of the breast M (step ST17), and the process ends.

In contrast, when it is determined by the body motion determining unit 37 that there is no body motion, the process proceeds to step ST17, where the reconstruction unit 34 reconstructs the two-dimensional image Hc and the processed projection images Gsfi other than the projection image Gc to generate a tomographic image of each of different slice planes of the breast M, and the process ends.

As described above, in the second embodiment, the projection image Gc corresponding to the radiation source position Sc is compared with the two-dimensional image Hc to determine whether or not there is a body motion, and if it is determined that there is a body motion, the body motion correction is performed on the two-dimensional image Hc based on the body motion. This allows removing a body motion of the subject during imaging between the projection image Gc corresponding to the radiation source position Sc and the two-dimensional image Hc to generate high image-quality tomographic images without blur.

Figure 13:
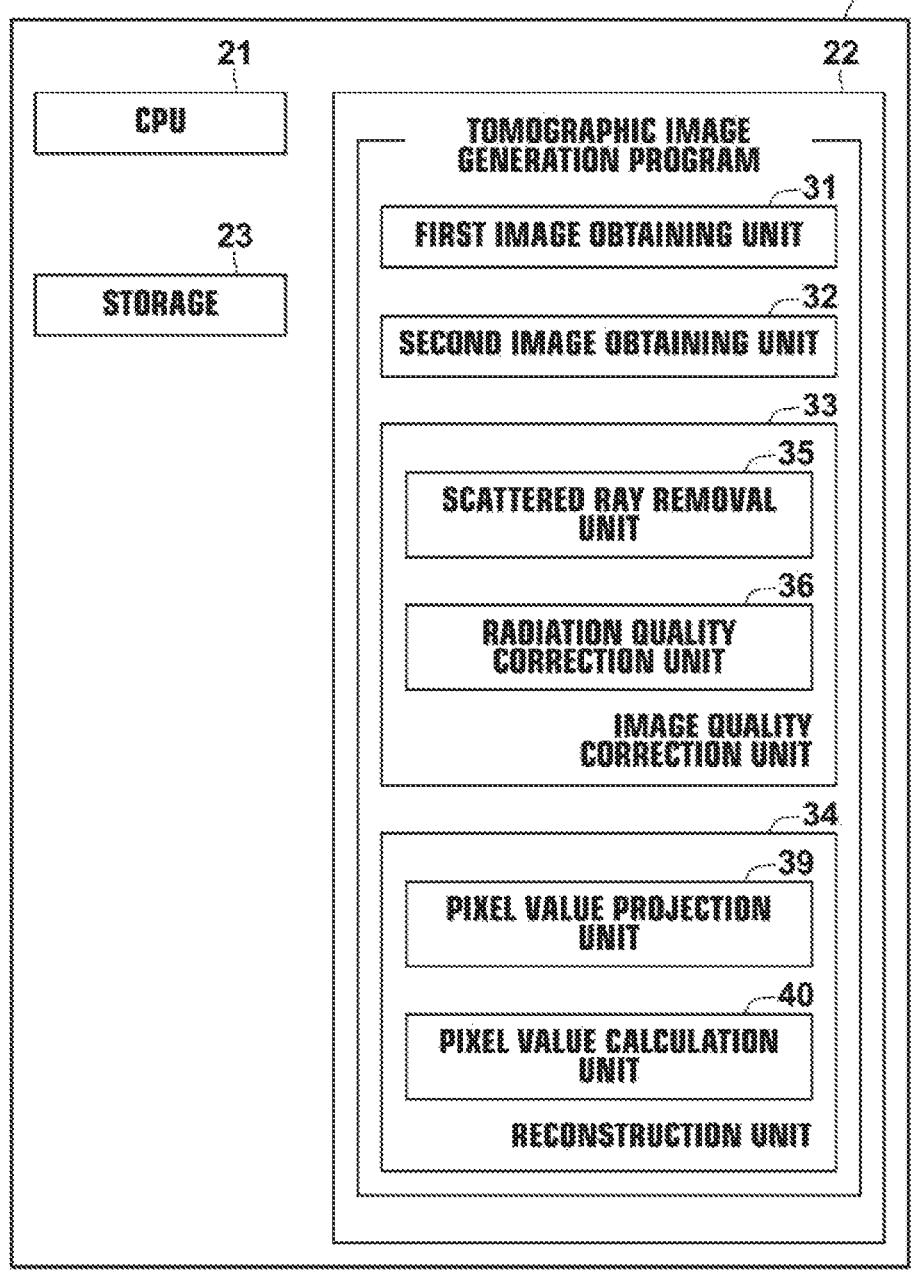
FIG. 13 is a diagram illustrating the schematic configuration of a tomographic image generation device of a third embodiment implemented by installing a tomographic image generation program on a computer.

Next, a third embodiment of the disclosure is described. FIG. 13 shows the schematic configuration of a radiographic imaging apparatus to which a tomographic image generation device according to a third embodiment of the disclosure is applied. It should be noted that features of the third embodiment that are the same as those in the first embodiment are assigned with the same reference numerals, and are not described in detail. As shown in FIG. 13, the difference between the third embodiment and the first embodiment lies in that the reconstruction unit 34 of the radiographic imaging apparatus 1 according to the third embodiment includes a pixel value projection unit 39 and a pixel value calculation unit 40. It should be noted that the reconstruction unit 34 of the second embodiment may also have the same configuration as that in the third embodiment.

Figure 14:
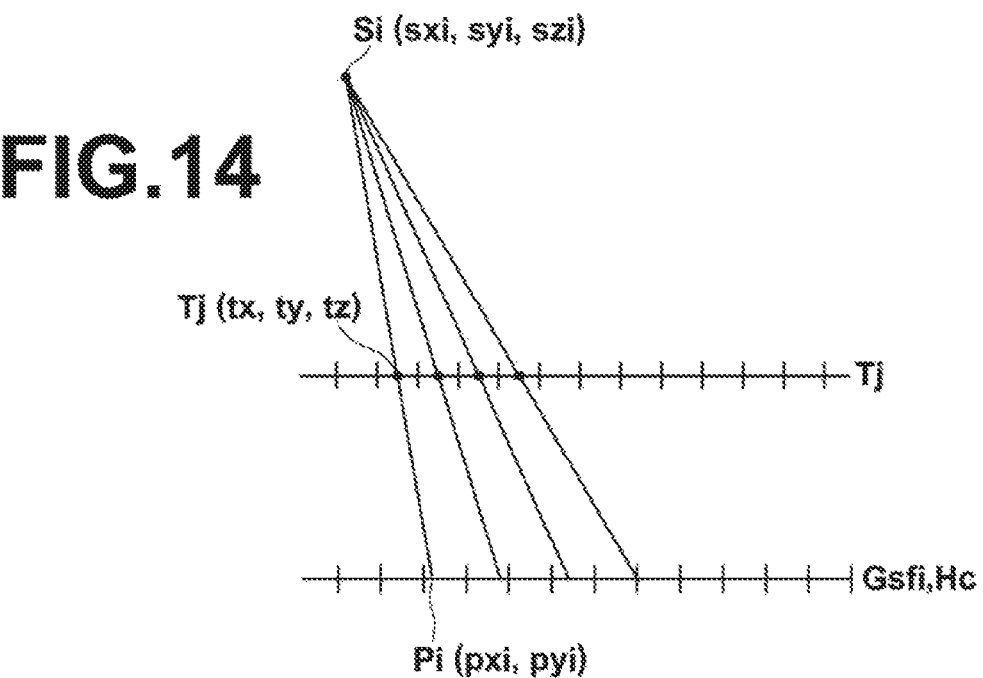
FIG. 14 is a diagram for explaining how pixel values are projected in the third embodiment.

The pixel value projection unit 39 projects pixel values of the processed projection images Gsfi and the two-dimensional image Hc at coordinate positions on a desired slice plane of the breast M while preserving the pixel values of the projection images Gsfi and the two-dimensional image Hc. FIG. 14 is a diagram for explaining how pixel values are projected. It should be noted that FIG. 14 explains a case where the projection images Gsfi which are obtained with the radiation source positions Si and the two-dimensional image Hc are projected on a desired slice plane Tj (j=1 to m, where m is the number of slice planes) of the breast M.

The projection images Gsfi and the two-dimensional image Hc and a tomographic image that is generated for each of the slice planes Tj as described later, are formed by a plurality of pixels which are two-dimensionally and discretely arranged at a given sampling interval, where the pixels are located at grid points corresponding to the given sampling interval. In FIG. 14, the short line segments orthogonally crossing the slice plane Tj and each of the projection images Gsfi and the two-dimensional image Hc represent boundary positions between the pixels. In FIG. 14, each center position between the pixel boundary positions is a pixel position, which is the grid point. As shown in FIG. 14, in the third embodiment, pixel values at positions on each of the projection images Gsfi and the two-dimensional image Hc intersecting with the straight lines that connect the radiation source position Si and the individual pixel positions on the slice plane Tj are projected as pixel values at the pixel positions on the slice plane Tj on the corresponding straight lines.

Assuming that coordinates of the radiation source position Si are (sxi, syi, szi), and coordinates of a pixel position on the slice plane Tj are Tj(tx, ty, tz), coordinates (pxi, pyi) of the corresponding coordinate position Pi on each of the projection images Gsfi and the two-dimensional image Hc are expressed by the equations (6) below. In this embodiment, the z-axis is set in the direction perpendicular to the detection surface of the radiation detector 15, the y-axis is set in the direction along the detection surface of the radiation detector 15 parallel to the direction in which the x-ray source 16 is moved, and the x-axis is set in the direction orthogonal to the y-axis.

$$pxi=(tx\times szi-sxi\times tz)/(szi-tz),$$

$$pyi=(ty\times szi-syi\times tz)/(szi-tz) \quad (6).$$

Figure 15:
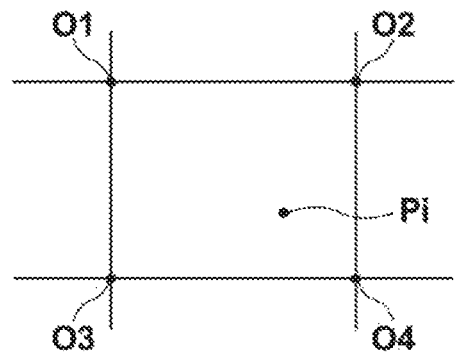
FIG. 15 is a diagram for explaining how a pixel value of a projection image is interpolated in the third embodiment.

It should be noted that there are cases where the coordinate position Pi on each of the projection images Gsfi and the two-dimensional image Hc is not a pixel position on the projection images Gsfi and the two-dimensional image Hc. For example, as shown in FIG. 15, a coordinate position Pi on any of the projection images Gsfi and the two-dimensional image Hc may be between four pixel positions O1 to O4 on the projection image Gsfi or the two-dimensional image Hc. In this case, interpolation is performed using pixel values at the four pixel positions O1 to O4, which are nearest to the coordinate position Pi of the projection image Gsfi or the two-dimensional image Hc, as shown in FIG. 15, to calculate the pixel value at the coordinate position Pi, and the calculated pixel value is projected on the pixel position (tx, ty, tz) on the slice plane Tj. As the interpolation, any technique, such as linear interpolation where the pixel values at the four pixel positions are weighted depending on the distance between the coordinate position Pi and each of the four pixel positions, non-linear bicubic interpolation using pixel values at more pixel positions around the coordinate position Pi, or B-spline interpolation, may be used. In place of performing the interpolation, the pixel value at the pixel position which is nearest to the coordinate position Pi may be used as the pixel value at the coordinate position Pi.

Figure 16:
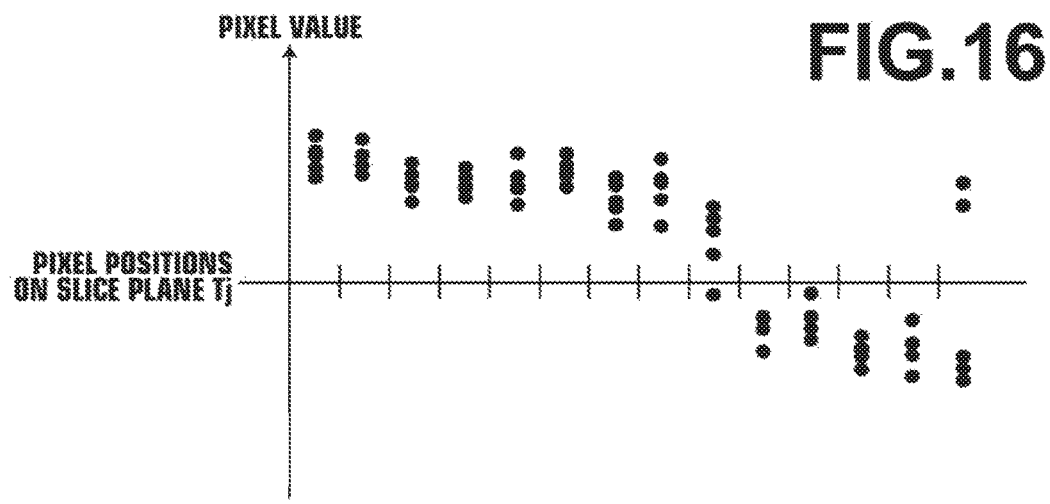
FIG. 16 is a diagram showing pixel values projected on a slice plane in the third embodiment.

The pixel value projecting unit 39 projects, for all the radiation source positions Si, the pixel values of the corresponding projection images Gsfi and the two-dimensional image Hc on the slice plane Tj. As a result, n pixel values corresponding to the number of the projected images are projected on each pixel position on the slice plane Tj, as shown in FIG. 16. FIG. 16 shows a state where pixel values of five images including four projection images Gsfi and the two-dimensional image Hc are projected on each pixel position for the purpose of explanation. In FIG. 16, and in FIGS. 17 and 18, which will be described later, the short line segments orthogonally crossing the slice plane Tj represent boundary positions between pixels, and the center positions between the pixel boundary positions are the pixel positions, which are the grid points.

The pixel value calculating unit 40 generates a tomographic image of the slice plane Tj by calculating each pixel value on the slice plane Tj. Specifically, the pixel value at each coordinate position of interest is calculated based on the pixel values of the projection images Gsfi and the two-dimensional image Hc projected in a predetermined range relative to the coordinate position of interest for which the pixel value is calculated. It should be noted that the coordinate position of interest may be a pixel position on the slice plane Tj. While the pixel values of the projection images Gsfi and the two-dimensional image Hc are projected on the pixel positions on the slice plane Tj in the third embodiment, the pixel value at each coordinate position of interest may be calculated using the pixel values projected on the coordinate position of interest, or without using the pixel values projected on the coordinate position of interest. Now, how the pixel value at each coordinate position of interest is calculated is described.

The pixel values of the projection images Gsfi and the two-dimensional image Hc projected on the slice plane Tj by the pixel value projecting unit 39 tend to be more similar when they are nearer to each other. Therefore the pixel value calculating unit 40 performs an operation to change the sharpness such that the pixel values projected on the slice plane Tj are smoothly continuous. In this embodiment, the pixel values projected on the slice plane Tj are filtered with a smoothing filter. Specifically, pixel values at pixel positions in a predetermined range, such as 3×3 or 5×5, with the coordinate position of interest being the center are filtered with a Gaussian filter, for example. This renders the pixel values of pixels at and around the coordinate position of interest smoothly continuous, thereby suppressing noise, such as quantum noise, which is originally included in the projection images Gsfi and the two-dimensional image H, in the pixel values projected on the slice plane Tj.

A value defining the size of the predetermined range may be stored as a fixed value in the storage 23. Further, the value may be changed arbitrarily according to input by the operator via the input unit 4. In this case, the value defining the size of the predetermined range stored in the storage 23 is rewritten according to input by the operator via the input unit 4 and the size of the predetermined range is changed.

The level of smoothness, i.e., the level of noise suppression can be changed by changing the filter size of the Gaussian filter. Specifically, increasing the filter size to increase the range of filtering with the coordinate position of interest being the center allows higher level of noise suppression. It should be noted that lower amounts of x-rays reaching the radiation detector 15 during imaging to obtain the projection images Gsfi and the two-dimensional image Hc result in more noise in the projection images Gsfi and the two-dimensional image Hc, which in turn results in more noise in the pixel values projected on the slice plane Tj. The amounts of noise in the projection images Gsfi and the two-dimensional image Hc also vary depending on the radiation quality of the x-rays, i.e., whether the x-rays are high voltage x-rays or low voltage x-rays. The amounts of noise in the projection images Gsfi and the two-dimensional image Hc also vary depending on the type of the radiation detector 15 used to take the projection images. Further, the projection images Gsfi are obtained without using the grid and the two-dimensional image Hc is obtained using the grid during imaging, and the amounts of noise in the projection images Gsfi and the two-dimensional image Hc also vary depending on the presence or absence of the grid or the type of the grid.

For this reason, in this embodiment, properties of the smoothing filter are changed based on the first and second imaging conditions. For example, for imaging conditions which result in more noise in the projection images Gsfi and the two-dimensional image Hc, the filter size is increased so that higher level of noise suppression is achieved.

When a Gaussian filter is used for the filtering, edges which are structures of the breast M included in a tomographic image which is generated as described later may be blurred. For this reason, the filtering may be performed using a bilateral filter which assigns neighboring pixels around the coordinate position of interest with weights depending on the distance between the pixels, and also assigns the neighboring pixels around the coordinate position of interest with normally distributed weights such that the weight is smaller when the difference between pixel values is greater. Alternatively, the filtering may be achieved using a non-local means filter which performs weighting based on similarity between a neighboring area around the coordinate position of interest on the slice plane Tj and a neighboring area around an arbitrary pixel on the slice plane Tj. This allows suppressing noise while preserving edges, thereby preventing lowering of the sharpness of a tomographic image which is generated as described later.

Further, the pixel values projected on the slice plane Tj may be filtered with a differential filter, for example, to detect an edge, which is the structure where there is a sudden change in the pixel value that exceeds a predetermined threshold value, and the filter properties may be changed such that the filtering is applied along the direction in which the edge extends, to thereby change the level of sharpness. Still further, the filtering may be performed such that, with respect to pixel values along a boundary of an edge, pixel values at positions beyond the edge are not used. This allows preventing the edge from being smoothed, thereby preventing lowering of the sharpness of the distribution of the pixel values projected on the slice plane Tj while suppressing noise.

In place of or in addition to the smoothing, an operation to emphasize the sharpness may be performed to emphasize edges. In this case, it is preferred to perform the operation to emphasize the sharpness along the direction in which each edge extends.

After the filtering is performed as described above, the pixel value calculating unit 40 performs regression analysis on the pixel values of the projection images Gsfi and the two-dimensional image Hc projected on the slice plane Tj to generate a curved surface, or a regression surface, that represents a tomographic image of the slice plane Tj. In the following description, the regression surface is considered as a regression curve for ease of explanation. The regression analysis is a statistical technique for analyzing a multivariate relationship. It is assumed here that observed values observed at observation points include noise added to the true values. The regression analysis is a technique to solve an inverse problem to find the true value at every observation point by a least squares method, a moving average method, regression using a kernel function, etc. In the third embodiment, a pixel value rm at each coordinate position of interest um is calculated by the regression analysis with assuming that each coordinate position on the slice plane Tj with the pixel values of the projection images Gsfi and the two-dimensional image Hc projected thereon is an observation point uk, each pixel value of the projection images Gsfi projected on the observation point uk is an observed value qk, and the pixel value calculated for the coordinate position of interest um is a true value rm.

Figure 17:
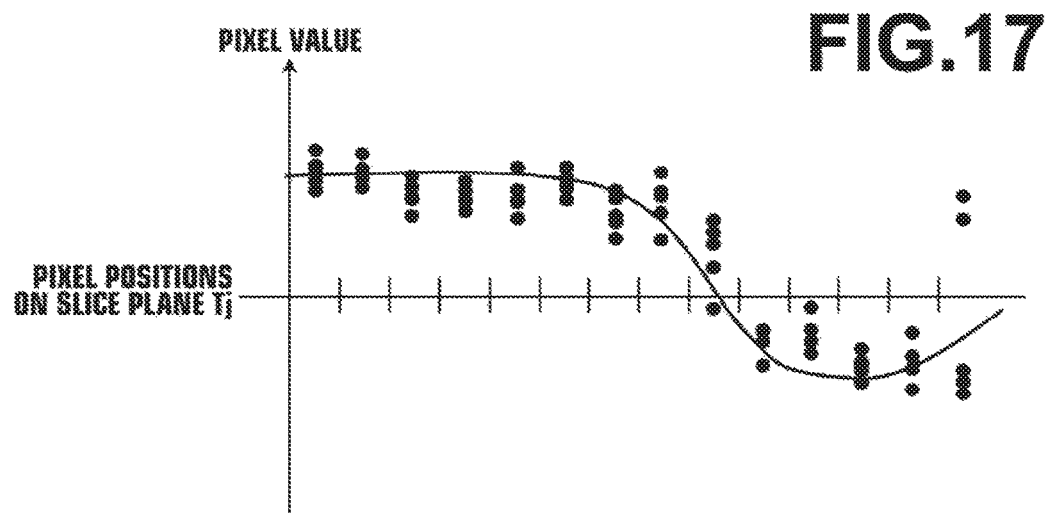
FIG. 17 is a diagram for explaining how a regression curve (regression surface) including outliers is generated in the third embodiment.

In the case where a least squares method is used, it is assumed that the true value follows a function whose distribution is defined by γ parameters a, i.e., r=f(u|a1, a2, . . . , aγ). Then, the function f can be determined by finding the parameters a1, a2, . . . , aγ which minimize squared errors between the true values and the observed values. Specifically, the pixel value rm at each coordinate position of interest is calculated by determining the parameters of the function f according to the equation (7) below, such that the total sum of errors of the observed values at the observation points is minimized, to generate the regression curve (regression surface). It should be noted that, as shown by the equation (8) below, a weight wk may be set for each observed value qk, and the regression curve (regression surface) may be generated by calculating the pixel value rm at each coordinate position of interest um by a weighted least squares method. The calculated regression curve (regression surface) is shown in FIG. 17.

$$r_m = \sum_k \{q_k - f(u_k)\}^2 \qquad (7)$$

$$r_m = \sum_k w_k \{q_k - f(u_k)\}^2 \qquad (8)$$

At this time, assigning the observed values qk of the two-dimensional image Hc with a weight larger than a weight assigned to the observed values qk of the projection images Gsfi allows increasing reliability of calculation of the regression curve (regression surface). It should be noted that, as the weight wk, for example, a weight of 5.0 may be assigned to the observed values qk of the two-dimensional image Hc, and a weight of 1.0 may be assigned to the observed values qk of the projection images Gsfi.

In the case where a moving average method is used, the regression surface is generated by calculating the pixel value at each coordinate position of interest by the moving average method. Specifically, considering the regression surface as a regression curve for ease of explanation, for the pixel value at each coordinate position of interest urn, an average value $\{(q_{k-1})+q_k+(q_{k+1})\}/3$ of the pixel values of the projection images Gsfi projected on three coordinate positions adjacent to the coordinate position of interest urn, i.e., coordinate positions uk−1, uk, and uk+1, for example, is calculated, and the calculated average value is used as the pixel value at the coordinate position of interest um. It should be noted that a weight may be set for each pixel value. For example, weights may be set such that the weight is smaller as the distance from the coordinate position of interest um is greater. Further, the observed values qk of the two-dimensional image Hc may be assigned with a weight larger than a weight assigned to the observed values qk of the projection images Gsfi.

In the case where regression using a kernel function is used, the regression curve (regression surface) is calculated by determining a kernel function, according to the equation (9) below, for each coordinate position of interest um and the observation points uk on the slice plane Tj on which the pixel values of the projection images Gsfi and the two-dimensional image Hc are projected. The "argmin" in the equation (9) means that the value of r(um) that minimizes the right side is calculated.

$$r(u_m) = \operatorname*{argmin}_{r(u_m)} \sum_k \{q_k - r(u_m)\}^2 \; K(u_k, u_m, q_k, q_m) \qquad (9)$$

In FIG. 16, two pixel values among the five pixel values projected on the rightmost pixel position on the slice plane Tj are largely different from the pixel values at the adjacent pixel position. If there are pixel values that are largely different from the pixel values of the adjacent pixels, the value of the generated regression surface at the pixel position which includes the outliers is largely different from the value at the adjacent pixel position, as shown in FIG. 17. Then, when a tomographic image is generated from the calculated regression surface, as described later, the tomographic image includes an artifact at the pixel position corresponding to the outliers.

For this reason, the pixel value calculating unit 40 determines a pixel value which is largely different from the adjacent pixel values among the pixel values projected on the slice plane Tj as an outlier, and calculates the pixel value at each coordinate position of interest with removing the outlier pixel value. For example, the pixel value calculating unit 40 calculates a difference between each of the pixel values projected on the coordinate position of interest and an average value of pixel values at pixel positions adjacent to the coordinate position of interest on the slice plane Tj, and determines a pixel value whose difference from the average value exceeds a predetermined threshold value as an outlier to remove the outlier pixel value when the regression analysis is performed. In place of removing the outlier, the outlier pixel value may be assigned with a small weight.

Figure 18:
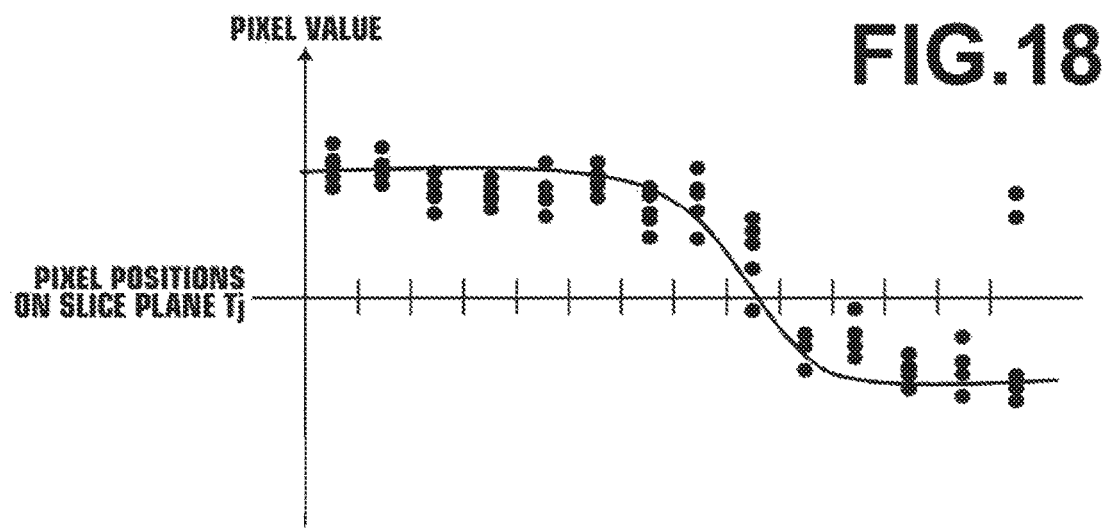
FIG. 18 is a diagram for explaining how a regression curve (regression surface) from which outliers are removed is generated in the third embodiment.

When the regression curve (regression surface) is calculated with removing the outliers or assigning the outliers with a small weight, the value at the pixel position including the outliers does not differ largely from the value at the adjacent pixel position, as shown in FIG. 18. This allows preventing the tomographic image from including an artifact.

The operation to remove an outlier can be integrated into the regression analysis. In the case where the least squares method is used, the weighted least squares method shown by the equation (8) above may be used with assigning the outlier pixel values with a weight of 0 or a small weight. In the case where the moving average is used, a weighted average may be calculated with assigning the outlier pixel values with a weight of 0 or a small weight.

Further, when the least squares method is used, it is preferred that, first, weights are determined such that outliers are assigned with a small weight, and after the outliers are removed, the observed values qk of the two-dimensional image Hc are assigned with a weight larger than a weight assigned to the observed values qk of the projection images Gsfi. At this time, in order to remove outliers that introduce artifacts, it is preferred to use information of images obtained with many radiation source positions, rather than using only an image that is obtained with one radiation source position. For this reason, it is preferred that a weight of the same value is used to remove outliers from the projection images Gsfi and the two-dimensional image Hc.

After the regression surface is generated, the pixel value calculating unit 40 samples the regression surface at a desired sampling interval to generate a tomographic image. The sampling interval may be stored in the storage 23 as a fixed value. The sampling interval may be changeable to an arbitrary value according to an instruction made via the input unit 4. For example, if the same sampling interval as that of the projection images Gsfi and the two-dimensional image Hc is set, the tomographic image has the same resolution as that of the projection images Gsfi and the two-dimensional image Hc. If the sampling interval is set smaller than that of the projection images Gsfi and the two-dimensional image Hc, the tomographic image has a higher resolution than that of the projection images Gsfi and the two-dimensional image Hc. In contrast, if the sampling interval is set greater than that of the projection images Gsfi and the two-dimensional image Hc, the tomographic image has a lower resolution than that of the projection images Gsfi and the two-dimensional image Hc. In this case, the value of the sampling interval stored in the storage 23 is rewritten according to input by the operator via the input unit 4 and the sampling interval is changed. Alternatively, the sampling interval may be adjusted depending on the resolution of the display unit 3.

Figure 19:
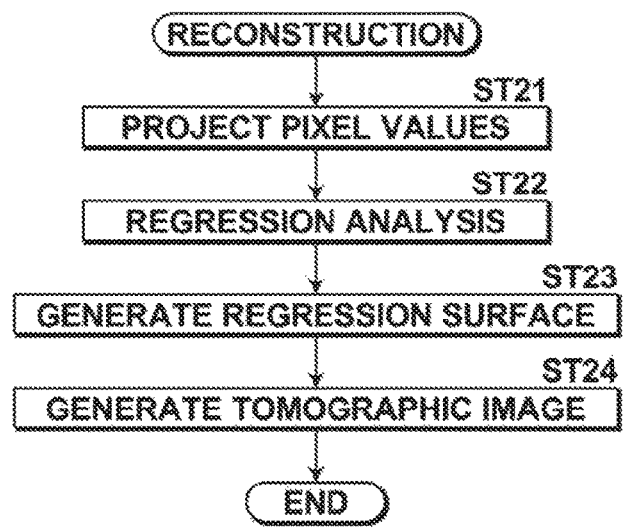
FIG. 19 is a flow chart showing the process performed in the third embodiment.

Next, the process performed in the third embodiment is described. FIG. 19 is a flow chart showing the process performed in the third embodiment. It should be noted that the difference between the third embodiment and the first and second embodiments lies only in the reconstruction operation, and only the reconstruction operation is described below. In the reconstruction operation, the pixel value projection unit 39 projects pixel values of the projection images Gsfi and the two-dimensional image Hc on coordinate positions on a desired slice plane Tj of the breast M, while preserving the pixel values of the projection images Gsfi and the two-dimensional image Hc (step ST21).

Then, the pixel value calculating unit 40 performs the regression analysis on the pixel values of the projection images Gsfi and the two-dimensional image Hc projected on the slice plane Tj (step ST22) to generate a regression surface that represents a tomographic image of the slice plane Tj (step ST23). Further, the pixel value calculating unit 40 samples the regression surface at a given sampling interval to generate a tomographic image (step ST24), and the process ends. It should be noted that, when another tomographic image of a different slice plane is generated, the operations in steps ST21 to ST24 are performed with changing the position of the slice plane.

As described above, in the third embodiment, pixel values of the projection images Gsfi and the two-dimensional image Hc are projected on coordinate positions on a desired slice plane Tj of the breast M, which is the subject, based on the positional relationship between the position of the x-ray source 16 corresponding to each of the projection images Gsfi and the two-dimensional image Hc and the radiation detector 15, while preserving the pixel values of the projection images Gsfi and the two-dimensional image Hc. Then, the pixel value at each coordinate position of interest is calculated by generating a regression surface by regression analysis, for example, based on the pixel values of the projection images Gsfi and the two-dimensional image Hc projected in a predetermined range relative to the coordinate position of interest on the slice plane Tj, to generate a tomographic image. When compared with the conventional techniques where only the pixel values of the projection images Gsfi and the two-dimensional image Hc projected on each coordinate position of interest are used to calculate the pixel value at the coordinate position of interest, this embodiment allows taking the influence of pixel values around the coordinate position of interest into account, thereby reducing artifacts to allow generation of a tomographic image with even higher image quality.

Further, a tomographic image with a desired resolution can be generated by sampling the regression surface at a desired sampling interval and calculating the pixel value at each coordinate position of interest.

Now, how the exposure dose is reduced in this embodiment is described. FIG. 20 shows a table for explaining the exposure dose in this embodiment. The table LUT3 shown in FIG. 20 shows T/F, tube voltage, radiation dose (mAs), the presence or absence of the grid, and AGD (mGy), which is an average mammary gland radiation dose, for simple imaging and 15-shot tomosynthesis imaging, respectively.

According to the table LUT3 shown in FIG. 20, when the tomosynthesis imaging is performed with all the radiation source positions and the simple imaging is performed, the total AGD is 2.50 mGy According to the table LUT3, the radiation dose per tomosynthesis imaging is about 2.7 mAs. This is equivalent to 0.1 mGy. In the case where the tomosynthesis imaging is not performed with the radiation source position Sc, as in the first and third embodiments, the radiation dose per tomosynthesis imaging can be reduced, and the total AGD when the tomosynthesis imaging and the simple imaging are performed becomes about 2.40 mGy. Thus, according to the first and third embodiments, reduction of the exposure dose of the breast M can be achieved.

Further, according to this embodiment, using the two-dimensional image Hc for the reconstruction allows improving image quality of the tomographic image, thereby allowing reduction of the radiation dose during tomosynthesis imaging. The present inventors have found through experiments that a radiation dose per tomosynthesis imaging reduced to 1.5 mAs (which is equivalent to 0.056 mGy) still allows generating tomographic images with sufficiently high image quality. In this case, the total AGD for 14-shot tomosynthesis imaging excluding the AGD for the simple imaging is 0.78 mGy, and the total AGD for the tomosynthesis imaging and the simple imaging is 1.78 mGy. Thus, significant reduction of the exposure dose can be achieved when compared to the case where the tomosynthesis imaging and the simple imaging are performed under the conditions shown in the table LUT3. It should be noted that assigning the two-dimensional image Hc with a weight during the reconstruction of tomographic images allows further reduction of the radiation dose per tomosynthesis imaging to further reduce the exposure dose.

It should be noted that, in the above-described embodiments, a pseudo image that appears as an image of a type that is different from the tomographic images ay be generated from the tomographic images. For example, an addition tomographic image may be generated as the pseudo image by adding up values at corresponding pixel positions of a plurality of tomographic images generated for a plurality of slice planes. The thus generated addition tomographic image shows a pseudo transmission image of the subject, which is the same as a two-dimensional image obtained by the simple imaging. In place of the addition tomographic image, a maximum projection image, which is obtained by an MIP method that extracts maximum values from the corresponding pixel positions of the plurality of tomographic images, may be generated as the pseudo image. Alternatively, a minimum projection image, which is obtained by a minIP method that extracts minimum values from the plurality of tomographic images, may be generated as the pseudo image.

Further, while the two-dimensional image Hc is subjected to the body motion correction if it is determined that there is a body motion, and the corrected two-dimensional image Hc and the projection images Gsfi are used for the reconstruction in the above-described second embodiment, the projection image Gc obtained with the radiation source position Sc may be subjected to the image quality correction similarly to the other projection images, and the reconstruction may be performed using only the processed projection images Gsfi.

Further, while the scattered ray removal and the radiation quality correction are performed as the image quality correction in the above-described embodiments, only one of the scattered ray removal and the radiation quality correction may be performed.

Further, in the above-described first and third embodiments, the tomosynthesis imaging is not performed with the radiation source position Sc where the optical axis of x-rays emitted from the x-ray source 16 is normal to the radiation detector 15. However, the radiation source position with which the tomosynthesis imaging is not performed may be one other than the radiation source position Sc where the optical axis of x-rays emitted from the x-ray source 16 is normal to the radiation detector 15. In this case, the simple imaging may be performed with the radiation source position with which the tomosynthesis imaging is not performed. When the simple imaging is performed, a grid of a type that is suitable for the radiation source position may be used.

Further, while the subject is the breast M in the above-described embodiments, this is not intended to limit the disclosure, and the subject may be any body site, such as the chest, the abdomen, etc., of a human body. In this case, during the above-described scattered ray removal, a subject thickness distribution is necessary to calculate the scattered ray content distribution S(x, y). The subject thickness distribution T(x, y) may be calculated by transforming pixel values of the projection images into thicknesses using a linear attenuation coefficient value, assuming that the luminance distributions of the projection images substantially agree with the subject thickness distribution. Alternatively, the subject thickness distribution may be obtained by measuring the thicknesses of the subject using a sensor, or the like, or may be approximated with a cubic or cylindroid model.

Now, advantageous effects of the embodiments of the disclosure are described.

In the case where at least one of the scattered ray removal and the radiation quality correction is performed as the image quality correction, if the scattered ray removal is performed, the scattered ray components can be removed from the first image. If the radiation quality correction is performed, the contrast of the first images can be made match the contrast of the second image. This allows achieving higher image quality of the tomographic images without being influenced by at least one of blur due to the scattered rays and the low contrast of the images.

The scattered rays during imaging occur in different manners depending on the radiation quality of radiation. In the case where the image quality correction includes the scattered ray removal and the radiation quality correction, if the radiation quality correction is performed first, the radiation quality correction has to be performed with taking the extent of scattered rays that occur depending on the radiation quality into account. It is, however, technically difficult to perform the radiation quality correction with taking the extent of scattered rays that occur depending on the radiation quality into account. For this reason, in the case where the image quality correction includes the scattered ray removal and the radiation quality correction, the image quality correction can be facilitated by performing the scattered ray removal before the radiation quality correction.

In the case where the given radiation source position is a radiation source position other than the different radiation source positions, it is not necessary to perform imaging to obtain a first image with the given radiation source position. This allows reducing the number of times of application of radiation to the subject, thereby allowing reduction of the exposure dose of the subject.

In the case where the different radiation source positions includes the given radiation source position, whether or not there is a body motion of the subject during imaging between the first image corresponding to the given radiation source position and the second image can be determined by comparing the first image corresponding to the given radiation source position with the second image. Then, if it is determined that there is no body motion, the first images having been subjected to the image quality correction, other than the first image corresponding to the given radiation source position, and the second image are reconstructed. This allows generating a high image-quality tomographic image without blur, with taking a body motion of the subject during imaging between the first and second images corresponding to the given radiation source position into account.

If it is determined that there is a body motion, the body motion correction is performed on the second image to correct for positional misalignment between the subject contained in the second image and the subject contained in the first image corresponding to the given radiation source position based on the body motion, and the first images having been subjected to the image quality correction, other than the first image corresponding to the given radiation source position, and the second image having been subjected to the body motion correction are reconstructed. This allows removing the body motion of the subject during imaging between the first and second images corresponding to the given radiation source position, thereby allowing generating high image-quality tomographic images without blur.

In the case where the first images having been subjected to the image quality correction and the second image are reconstructed with assigning the second image with a larger weight than a weight assigned to the first images having been subjected to the image quality correction, the reconstruct can be performed with higher influence of the two-dimensional image, which has higher image quality. This allows achieving higher image quality of the tomographic images and further reduction of the exposure dose of the subject.

In the case where pixel values of the first images having been subjected to the image quality correction and the second image are projected on coordinate positions on a desired slice plane of the subject based on a positional relationship between the detecting unit and the radiation source position during imaging corresponding to each of the first images having been subjected to the image quality correction and the second image, while preserving the pixel values of the first and second images, and a pixel value at each coordinate position of interest is calculated based on the pixel values of the first images having been subjected to the image quality correction and the second image and projected in a predetermined range relative to the coordinate position of interest on the slice plane to thereby generate a tomographic image, influence of pixel values around the coordinate position of interest can be taken into account, unlike the conventional techniques where the pixel value at each coordinate position of interest is calculated using only pixel values of the first images having been subjected to the image quality correction and the second image and projected at the coordinate position of interest. This allows reducing artifacts to generate a tomographic image with higher image quality.

In the case where the pixel values at the pixel positions on the slice plane are calculated by performing the regression analysis to generate a regression surface that represents a tomographic image of the slice plane, and sampling the regression surface at a desired sampling interval, a tomographic image with a desired resolution can be generated.

What is claimed is:

1. A tomographic image generation device comprising:
at least one hardware processor configured to implement:
a first image obtaining unit for obtaining a plurality of first images corresponding to different radiation source positions, the first images being imaged by moving a radiation source relative to a detecting unit and applying radiation to a subject from the different radiation source positions to which the radiation source is moved under a first imaging condition for tomosynthesis imaging;

a second image obtaining unit for obtaining a second image imaged by applying the radiation to the subject from a given radiation source position under a second imaging condition for simple imaging;

an image quality correction unit for performing image quality correction on the first images to compensate for a difference of image quality between the first images and the second image based on a difference between the first imaging condition and the second imaging condition; and a reconstruction unit for reconstructing the first images having been subjected to the image quality correction and the second image to generate a tomographic image of a slice plane of the subject, wherein the image quality correction includes at least one of scattered ray removal for removing, from the first images, scattered ray components contained in radiation transmitted through the subject when imaging under the first imaging condition is performed, and radiation quality correction for correcting for a difference of contrast between the first images and the second image due to a difference between radiation quality of the first imaging condition and radiation quality of the second imaging condition, and wherein the image quality correction includes the scattered ray removal and the radiation quality correction, and wherein the image quality correction unit performs the scattered ray removal before the radiation quality correction.

2. The tomographic image generation device as claimed in claim 1, wherein the given radiation source position is a radiation source position where the optical axis of the radiation from the radiation source is normal to the detection unit.

3. The tomographic image generation device as claimed in claim 1, wherein the given radiation source position is a radiation source position other than the different radiation source positions.

4. The tomographic image generation device as claimed in claim 1, wherein the different radiation source positions include the given radiation source position.

5. The tomographic image generation device as claimed in claim 4, further comprising a body motion determining unit for determining whether or not there is a body motion of the subject during imaging between the first image corresponding to the given radiation source position and the second image by comparing the first image corresponding to the given radiation source position with the second image, wherein, if it is determined that there is no body motion, the reconstruction unit generates the tomographic image by reconstructing the first images having been subjected to the image quality correction, other than the first image corresponding to the given radiation source position, and the second image.

6. The tomographic image generation device as claimed in claim 5, wherein, if it is determined that there is a body motion, the reconstruction unit performs, on the second image, body motion correction for correcting for positional misalignment between the subject contained in the second image and the subject contained in the first image corresponding to the given radiation source position based on the body motion, and generates the tomographic image by reconstructing the first images having been subjected to the image quality correction, other than the first image corresponding to the given radiation source position, and the second image having been subjected to the body motion correction.

7. The tomographic image generation device as claimed in claim 1, wherein the reconstruction unit reconstructs the first images having been subjected to the image quality correction and the second image with assigning a larger weight to the second image than a weight assigned to the first images having been subjected to the image quality correction.

8. The tomographic image generation device as claimed in claim 1, wherein the reconstruction unit comprises:

a pixel value projection unit for projecting pixel values of the first images having been subjected to the image quality correction and the second image onto coordinate positions on the slice plane of the subject based on a positional relationship between the detection unit and the radiation source position during imaging corresponding to each of the first images having been subjected to the image quality correction and the second image, while preserving the pixel values of the first images having been subjected to the image quality correction and the second image, and a pixel value calculation unit for calculating a pixel value at each coordinate position of interest based on the pixel values of the first images having been subjected to the image quality correction and the second image projected in a predetermined range relative to the coordinate position of interest on the slice plane to generate the tomographic image of the slice plane.

9. The tomographic image generation device as claimed in claim 8, wherein the pixel value calculating unit calculates the pixel value at the coordinate position of interest by performing regression analysis on the pixel values of the first images having been subjected to the image quality correction and the second image projected on the slice plane.

10. A tomographic image generation method comprising the steps of:

obtaining a plurality of first images corresponding to different radiation source positions, the first images being imaged by moving a radiation source relative to a detecting unit and applying radiation to a subject from the different radiation source positions to which the radiation source is moved under a first imaging condition for tomosynthesis imaging;

obtaining a second image imaged by applying the radiation to the subject from a given radiation source position under a second imaging condition for simple imaging;

performing image quality correction on the first images to compensate for a difference of image quality between the first images and the second image based on a difference between the first imaging condition and the second imaging condition; and reconstructing the first images having been subjected to the image quality correction and the second image to generate a tomographic image of a slice plane of the subject, wherein the image quality correction includes at least one of scattered ray removing for removing, from the first images, scattered ray components contained in radiation transmitted through the subject when imaging under the first imaging condition is performed, and radiation quality correction for correcting for a difference of contrast between the first images and the second image due to a difference between radiation quality of the first imaging condition and radiation quality of the second imaging condition, and wherein the image quality correction includes the scattered ray removal and the radiation quality correction, and wherein the image quality correction unit performs the scattered ray removal before the radiation quality correction.

11. A non-transitory recording medium having recorded thereon a tomographic image generation program for causing a computer to execute the steps of:

obtaining a plurality of first images corresponding to different radiation source positions, the first images being imaged by moving a radiation source relative to a detecting unit and applying radiation to a subject from the different radiation source positions to which the radiation source is moved under a first imaging condition for tomosynthesis imaging;

obtaining a second image imaged by applying the radiation to the subject from a given radiation source position under a second imaging condition for simple imaging;

performing image quality correction on the first images to compensate for a difference of image quality between the first images and the second image based on a difference between the first imaging condition and the second imaging condition; and reconstructing the first images having been subjected to the image quality correction and the second image to generate a tomographic image of a slice plane of the subject, wherein the image quality correction includes at least one of scattered ray removal for removing, from the first images, scattered ray components contained in radiation transmitted through the subject when imaging under the first imaging condition is performed, and radiation quality correction for correcting for a difference of contrast between the first images and the second image due to a difference between radiation quality of the first imaging condition and radiation quality of the second imaging condition, and wherein the image quality correction includes the scattered ray removal and the radiation quality correction, and wherein the image quality correction unit performs the scattered ray removal before the radiation quality correction.

12. The tomographic image generation device as claimed in claim 1, wherein the first and second imaging conditions include materials forming an anode and a filter forming the radiation source, tube voltage, and information indicating the presence or absence of a scattered ray removing grid.

* * * * *